US012753290B1

(12) United States Patent
Kent et al.

(10) Patent No.: US 12,753,290 B1
(45) Date of Patent: Oct. 6, 2026

(54) DEPOLYMERIZATION OF POLYOLEFINS FOR BIOLOGICAL CONVERSION

(71) Applicant: National Technology & Engineering Solutions of Sandia, LLC, Albuquerque, NM (US)

(72) Inventors: Michael S. Kent, Albuquerque, NM (US); Daniella Victoria Martinez, Albuquerque, NM (US); Amit Kumar Jha, Mountain House, CA (US); Jose Alberto Rodriguez Ruiz, Concord, CA (US); Oleg Davydovich, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 400 days.

(21) Appl. No.: 18/231,543

(22) Filed: Aug. 8, 2023

Related U.S. Application Data

(60) Provisional application No. 63/396,324, filed on Aug. 9, 2022.

(51) Int. Cl.
*C08J 11/16* (2006.01)
*C12N 1/14* (2006.01)
*C12N 1/20* (2006.01)

(52) U.S. Cl.
CPC ................. *C08J 11/16* (2013.01); *C12N 1/14* (2013.01); *C12N 1/20* (2013.01); *C08J 2323/06* (2013.01)

(58) Field of Classification Search
CPC .... C08J 11/10; C08J 11/16; C08F 8/36; C08F 8/34
See application file for complete search history.

(56) References Cited

FOREIGN PATENT DOCUMENTS

WO 2022232189 A1 11/2022

OTHER PUBLICATIONS

Hu, ACS EST Engg. 2022, 2, 110-120 (Year: 2021).*
Chow, Chem. Eur. J., 2016, vol. 22, p. 9513-9518 and S1-S5 (Year: 2016).*
Discovery Report: The future of plastic. Published by C&EN. Q1 2020. 28 pages.
Areskogh, Dimitri, et al. "Chemical Pulping: Fenton's reaction: a simple and versatile method to structurally modify commercial lignosulphonates." Nordic Pulp and Paper Research Journal. Vol. 26, No. 1, 2011. pp 90-99. Published Jan. 2011. 9 pages.
Beckham, Gregg T., et al. "Opportunities and challenges in biological lignin valorization," Curr Opin Biotechnol. Dec. 2016; 42: 40-53. doi: 10.1016/j.copbio.2016.02.030. Published Mar. 11, 2016. 17 pages.

(Continued)

*Primary Examiner* — Robert C Boyle
(74) *Attorney, Agent, or Firm* — Cantor Colburn; Samantha Updegraff

(57) ABSTRACT

A method for depolymerizing polyolefins. The method includes a sulfonation step including contacting a polyolefin with a sulfonating agent in the absence of an organic solvent to provide a sulfonated polyolefin and a bond cleavage step including contacting a metal catalyst and an oxidant with the sulfonated polyolefin. A carbon-carbon bond of the sulfonated polyolefin is cleaved to provide a bioavailable carbon product wherein the bioavailable carbon product is a carbon source for microbial growth.

16 Claims, 11 Drawing Sheets

(56) References Cited

OTHER PUBLICATIONS

Chow, Cheuk-Fai, et al., "Combined Chemical Activation and Fenton Degradation to Convert Waste Polyethylene into High-Value Fine Chemicals." Chem. Eur. J. 2016, vol. 22, 9513-9518. Published May 11, 2016. 6 pages.

Feng, Hui-Min, et al. "Photo-assisted Fenton degradation of polystyrene." Environmental Science & Technology. vol. 45, No. 2, 2011. pp. 744-750. Published Dec. 15, 2010. 7 pages.

Krueger, Martin C., et al. "Potential of Wood-Rotting Fungi to Attack Polystyrene Sulfonate and Its Depolymerisation by Gloeophyllum trabeum via Hydroquinone-Driven Fenton Chemistry." PLoS ONE 10(7): e0131773. Published Jul. 6, 2015. 17 pages.

Linger, Jeffrey G., et al. "Lignin valorization through integrated biological funneling and chemical catalysis." PNAS. vol. 111; No. 33. 12013-12018. Published Aug. 19, 2014. 6 pages.

Martinez, Daniella V., et al. "Depolymerization of lignin for biological conversion through sulfonation and chelator-mediated Fenton reaction." Green Chemistry. vol. 24. The Royal Society of Chemistry. 2022. 1627-1643. Published Jan. 31, 2022. 17 pages.

Phongpreecha, T., et al. "Predicting lignin depolymerization yields from quantifiable properties using fractionated biorefinery lignins." Royal Society of Chemistry. Green Chem., 2017, 19, 5131-5143. Published Sep. 27, 2017. 13 pages.

* cited by examiner

DEPOLYMERIZATION OF POLYOLEFINS FOR BIOLOGICAL CONVERSION

CROSS-REFERENCE TO RELATED PATENT APPLICATIONS

This application claims priority to U.S. Provisional Patent Application Ser. No. 63/396,324, filed on Aug. 9, 2022, the content of which in its entirety is herein incorporated by reference.

STATEMENT OF GOVERNMENT INTEREST

This invention was made with Government support under Contract No. DE-NA0003525 awarded by the United States Department of Energy/National Nuclear Security Administration. The U.S. Government has certain rights in the invention.

BACKGROUND OF THE INVENTION

1. Field of the Invention

The present invention relates to a system and method for depolymerization of polyolefins for bioconversion through sulfonation followed by a bond cleavage reaction.

2. Description of the Related Art

Generating value from waste polyolefins through depolymerization and biological conversion to valuable fuels, chemicals, or intermediates has been limited by several factors including lack of cost effective depolymerization methods, toxicity within the breakdown products, and low bioconversion of the breakdown products.

A need remains for methods of depolymerizing polyolefins to efficiently and cost-effectively cleave carbon-carbon bonds to provide biologically available products.

SUMMARY OF THE INVENTION

In an embodiment, a method for depolymerizing polyolefins includes a sulfonation step including contacting a polyolefin with a sulfonating agent in the absence of an organic solvent to provide a sulfonated polyolefin and a bond cleavage step including contacting a metal catalyst and an oxidant with the sulfonated polyolefin, wherein a carbon-carbon bond of the sulfonated polyolefin is cleaved to provide a bioavailable carbon product. The bioavailable carbon product is a carbon source for microbial growth.

In another embodiment, a bioavailable carbon product is manufactured by depolymerization of polyolefins. The depolymerization of polyolefins includes contacting a polyolefin with a sulfonating agent in the absence of an organic solvent to provide a sulfonated polyolefin and contacting a metal catalyst and an oxidant with the sulfonated polyolefin. A carbon-carbon bond of the sulfonated polyolefin is cleaved to provide the bioavailable carbon product as a soluble organic material.

The foregoing features and elements may be combined in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION OF THE DRAWINGS

The present disclosure is illustrated by way of example and not limited in the accompanying figures in which like reference numerals indicate similar elements.

DETAILED DESCRIPTION OF THE INVENTION

Figure 1:
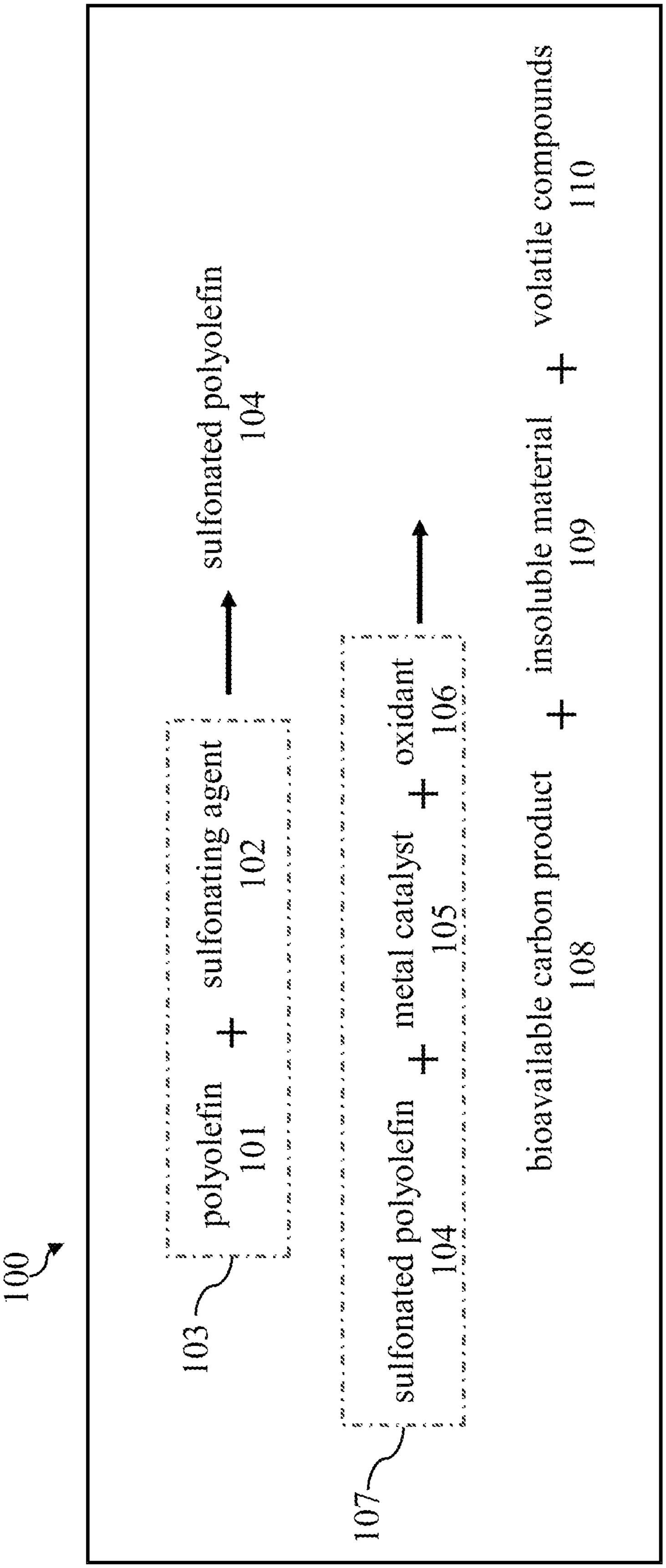
FIG. 1 is a flow diagram illustrating an embodiment of a polyolefin depolymerization method.

Disclosed herein is a method of depolymerizing polyolefins to provide biologically available carbon materials. The depolymerization method comprises a sulfonation step followed by a bond cleavage step. In an embodiment, the polyolefin depolymerization method comprises a sulfonation step (sulfonation reaction) including contacting a polyolefin with a sulfonating agent to provide a sulfonated polyolefin. The sulfonation step can be followed by a bond cleavage step (bond cleavage reaction) including contacting a sulfonated polyolefin with a metal catalyst and an oxidant. During the bond cleavage step, a carbon-carbon bond in the sulfonated polyolefin is cleaved. After the bond cleavage step, a bioavailable carbon product can be isolated.

The depolymerization method is applicable to a range of polyolefin starting materials. Carbon conversion into gas by-products ("carbon loss") during the depolymerization method can be reduced by selecting the disclosed component ratios for a sulfonating agent, a metal catalyst, and/or an oxidant. In some embodiments, the sulfonation step provides a sulfonated polyolefin. Treatment of the sulfonated polyolefin in the presence of a metal catalyst and oxidant (e.g., a Fenton reaction or a Fenton-like reaction) cleaves carbon-carbon bonds in the sulfonated polyolefin. In some embodiments, during the bond cleavage step, the metal catalyst can be added to an aqueous dispersion of the sulfonated polyolefin to provide a metal-loaded sulfonated polyolefin, followed by addition of the oxidant without removal of unbound, excess metal catalyst. In other embodiments, during the bond cleavage step, the metal catalyst can be added to an aqueous dispersion of the sulfonated polyolefin to provide a metal-loaded sulfonated polyolefin and the metal-loaded sulfonated polyolefin can be separated from the aqueous medium by filtration, rinsed with water to remove excess (unbound) metal catalyst, and dried prior to addition of the oxidant. Products of the bond cleavage step include a bioavailable carbon product including fully and/or partially depolymerized soluble organic materials.

The bioavailable carbon product of the depolymerization method can include organic compounds with one or more functional groups including a carboxylic acid, a hydroxyl group, a sulfonic acid group, and combinations thereof. The bioavailable carbon product of the depolymerization process can be utilized by microorganisms (e.g., anaerobic bacteria, aerobic bacteria, anaerobic fungi and aerobic fungi) as a sole carbon source and/or a supplemental carbon source.

The terminology used herein is for the purpose of describing particular embodiments only and is not intended to be limiting of the present disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

"And/or" includes any and all combinations of one or more of the associated listed items.

FIG. 1 is a flow diagram illustrating an embodiment of a polyolefin depolymerization method 100 (hereinafter method 100). The method 100 initiates with a polyolefin 101. The polyolefin 101 is contacted with a sulfonating agent 102 during a sulfonation step 103 and is converted into a sulfonated polyolefin 104. The sulfonated polyolefin 104 is contacted with a metal catalyst 105 and an oxidant 106 during a bond cleavage step 107. After completion of the bond cleavage step 107, the product mixture can be separated to provide a bioavailable carbon product 108, an insoluble material 109, and volatile compounds 110.

The method 100 can be used to depolymerize a wide range of polyolefins to provide bioavailable carbon products, such as low molecular weight organic compounds (e.g., molecular weights of 100 g/mol to 1000 g/mol). The bioavailable carbon products can be biologically available as a sole carbon source for microbial growth. In some embodiments, the method 100 can be applied to sulfonate and cleave carbon-carbon (C—C) bonds in the absence of an adjacent functional groups such as an ester, ether, alcohol, halogen, alkenyl group, alkynyl group, aryl group, and so forth. Furthermore, the method 100 can be applied to depolymerize polyolefins lacking any of the aforementioned functional groups. Depolymerization of polyolefins in the absence of any functional groups is particularly difficult due to the higher bond disassociation of the unactivated C—C and C—H bonds.

The extent of depolymerization of the method 100 impacts the biological availability of the resultant organic products. Insufficient depolymerization yields increased concentrations of high molecular weight organic compounds (e.g., molecular weights greater than or equal to 1000 grams per mole (g/mol)), which provide a less accessible carbon food source for microorganisms than low molecular weight organic compounds. Excessive depolymerization provides increased concentrations of volatile compounds (e.g., carbon dioxide), which are also a less accessible carbon food source for microorganisms. Accordingly, judicious selection of reagent molar ratios in the method 100 can balance the extent of depolymerization to maximize soluble, bioavailable carbon products while minimizing the amount of carbon lost as volatile compounds. The reagent molar ratios to maximize the yield of bioavailable carbon products and minimize the loss of carbon as volatile compounds for the method 100 are also described herein. In some embodiments, the method 100 converts less than about 60% of the total carbon in the polyolefin 101 into carbon dioxide, less than about 50% of the carbon into $CO_2$, less than about 40% of the carbon into $CO_2$, less than about 30% of the carbon into $CO_2$.

The polyolefin 101 can be a blend of polymers, copolymers, terpolymers, or combinations thereof. The polyolefin 101 can also be a homopolymer, a copolymer, a block copolymer, an alternating block copolymer, a random polymer, a random copolymer, a random block copolymer, or a combination of the foregoing polymers. In some embodiments, the polyolefin 101 can be a linear or a branched polyolefin. Suitable polyolefins include high-density polyethylene, low-density polyethylene, poly(vinyl chloride), polybutene, polymethylpentene, polypropylene, polystyrene, or combinations thereof. In some embodiments, the polyolefin 101 can be selected from unfunctionalized polyolefins such as high-density polyethylene, low-density polyethylene, polybutene, polymethylpentene, polypropylene, or combinations thereof. In some embodiments, the polyolefin 101 is polyethylene or polypropylene. In some embodiments, the polyolefin 101 is high density or low-density polyethylene. The polyolefin 101 can have a molecular weight of about 1,000 grams per mole (g/mol) to about 1,000,000 g/mol as measured by gel permeation chromatography in accordance with ASTM D6474.

The polyolefin 101 is contacted with a sulfonating agent 102 during a sulfonation step 103. The sulfonation step 103 can be performed in water, in aqueous buffers, or in the concentrated sulfonating agent 102 without further dilution. In some embodiments, the sulfonation step 103 is performed in the absence of organic solvents (e.g., acetonitrile, chloroform, dichloromethane, and the like).

In some embodiments, the sulfonating agent 102 is a sulfur oxo acid. Suitable sulfur oxo acids include fuming sulfuric acid, sulfuric acid, polysulfuric acids, dithionic acid, and combinations thereof. In some embodiments, the sulfonating agent 102 is fuming sulfuric acid. In the sulfonation step 103, the sulfonating agent 102 can have a concentration of about 10 weight percent (wt %) to about 99.9 wt % or about 20 wt % to about 90 wt %.

The temperature of the sulfonation step 103 can be about 20° C. to about 90° C. The reaction time of the sulfonation step 103 can be about 1 minute to about 10 hours, about 10 minutes to about 3 hours, about 30 minutes to about 6 hours. In some embodiments, the sulfonation step 103 provides less than about 20% of the carbon as carbon dioxide based on the total carbon in the polyolefin 101 starting material. In some embodiments, the sulfonation step 103 provides less than about 15% of the carbon as $CO_2$, less than about 10% of the carbon as $CO_2$, or less than about 5% of the carbon as $CO_2$ based on the total carbon in the polyolefin 101 starting material.

The sulfonation step 103 provides a sulfonated polyolefin 104. The sulfonated polyolefin 104 contains a polyolefin with a sulfonate group bonded to a carbon atom. In some embodiments, the sulfonated polyolefin 104 can contain multiple sulfonate groups. The presence of a sulfonate group on a carbon atom facilitates the scission of a C—C bond during the bond cleavage step 107. In some embodiments, the sulfonate group on a carbon atom facilitates scission of a C—C bond connected to an alpha, a beta, and/or a gamma adjacent carbon. In some embodiments, the C/S molar ratio of the sulfonated polyolefin is about 20 to about 3 or about 17 to about 5 (where C is the moles of carbon and S is the moles of sulfur present in the sulfonated polyolefin 104). As the C/S ratio of the sulfonated polyolefin decreases, the percentage of C recovered as water-soluble products after the bond cleavage step 107 increases. However, if the C/S ratio is lower than about 4, the sulfonated polyolefin partially dissolves and cannot be readily separated from the mixture by a simple technique such as filtration. When the C/S molar ratio of the sulfonated polyolefin is greater than about 4, the sulfonated polyolefin 104 can be readily separated from the reaction mixture. For example, the sulfonated polyolefin 104 can be separable from the reaction mixture by gravity filtration or filtration via water aspiration (vacuum pressure of about 10 torr). The separated sulfonated polyolefin 104 solids can be rinsed with water, alcohols, or mixtures thereof.

The bond cleavage step 107 can be performed by contacting the sulfonated polyolefin 104 with a metal catalyst 105 and an oxidant 106 to cleave C—C bonds. In the bond cleavage step 107, the initial concentration of the sulfonated polyolefin 104 can be about 1 mg/mL to about 100 mg/mL, about 2 mg/mL to about 50 mg/mL, or about 5 mg/mL to about 20 mg/mL. During the bond cleavage step 107, the metal catalyst 105 can serve to generate reactive oxygen species that activate a carbon-carbon bond for cleavage and the oxidant 106 can be fully or partially added to the carbons of the breaking carbon-carbon bond.

The metal catalyst 105 can be a multivalent metal salt. For example, the metal catalyst 105 can be a Fe(II) salt, a Fe(III) salt, a Cu(I) salt, a Cu(II) salt, a Cu(III) salt, a Mn(II) salt, a Mn(III) salt, or a combination thereof. Suitable salts include sulfates, nitrates, chlorides, bromides, oxalates, or combinations thereof. The initial concentration of the metal catalyst 105 can be about 0.1 mM to about 50 mM, about 1 mM to about 25 mM. The metal to sulfur (M/S) molar ratio of the bond cleavage step 107, (where M is the moles of metal present in the metal catalyst 105 and S is the moles of sulfur present in the sulfonated polyolefin 104), can be about 0.01 to about 2 or about 0.02 to about 1.

The oxidant 106 can be hydrogen peroxide ($H_2O_2$), molecular oxygen ($O_2$), or a combination thereof. In some embodiments, the oxidant 106 is hydrogen peroxide. The oxidant 106 can have a concentration of 0.1 wt % to about 10 wt % or about 0.5 wt % to about 5 wt %. The oxidant 106 to monomer molar ratio, (where the oxidant is the moles of oxidant in the oxidation step and the monomer is the moles of monomer in the polyolefin 101 starting material), can be about 1 to about 10 or about 1.5 to about 4.

The reaction time of the bond cleavage step 107 can be about 1 minute to about 24 hours, about 10 minutes to about 12 hours, or about 30 minutes to about 6 hours. The temperature of the bond cleavage step 107 can be about 20° C. to about 90° C.

In some embodiments, during the bond cleavage step 107, after incubating the sulfonated polyolefin 104 with the metal catalyst 105 and the oxidant 106, additional metal catalyst 105 and/or oxidant 106 can be charged to the reaction mixture. In other embodiments, the charging of additional metal catalyst 105 and/or oxidant 106 to the reaction mixture can be repeated one to five times. The concentration of additional metal catalyst 105 and the oxidant 106 can be 0.1 mM to about 50 mM and 0.1 wt % to about 10 wt %, respectively.

Suitable solvents for the bond cleavage step 107 can be water, aqueous buffers, or combinations thereof. In some embodiments, the solvent for the bond cleavage step 107 is water. In some embodiments, the bond cleavage step 107 is performed in the absence of organic solvents. The pH of the bond cleavage reaction mixture can be about 2 to about 10, about 3 to about 7.

Carbon-carbon bonds cleaved during the bond cleavage step 107 can be single or double carbon bonds. Products from carbon-carbon bond cleavage can be molecules of the same or different molecular weight. In some embodiments, a portion of the carbon contained in the sulfonated polyolefin 104 can be converted to a volatile compound 110 (e.g., $CO_2$). In some embodiments, the products of the bond cleavage step 107 are $CO_2$, a bioavailable carbon product 108, and an insoluble material 109. In some embodiments, the bond cleavage step 107 converts less than about 60% of the total carbon in the polyolefin 101 into $CO_2$, less than about 50% of the carbon into $CO_2$, less than about 40% of the carbon into $CO_2$. In some embodiments, the yield of bioavailable soluble product 108 can be optimized by judicious selection of the C/S ratio, the M/S molar ratio, and the oxidant/monomer molar ratio. For example, a C/S ratio of 5, a M/S molar ratio of 0.3, and an oxidant/monomer molar ratio of 2.6 provides 41% of the carbon in the polyolefin 101 starting material as the soluble product (soluble organic material). In comparison, a C/S ratio of 17, a M/S molar ratio of 0.02, and a oxidant/monomer molar ratio of 1.4 provides only 21% of the carbon in the polyolefin 101 starting material as soluble product.

Separation of the soluble bioavailable carbon product 108 and the insoluble material 109 from the bond cleavage reaction mixture can be performed by filtration, dialysis, decanting, centrifugation, or other suitable techniques. In some embodiments, the bioavailable carbon product 108 is not isolated before biological conversion but is charged directly into a bioreactor. In some embodiments, the reaction mixture can be adjusted to a desired pH before charging into a bioreactor.

The method 100 provides efficient depolymerization of the polyolefin 101 where the total mass of the bioavailable carbon product 108 can include about 20 wt % to about 80 wt % or about 40 wt % to about 60 wt % of the total carbon contained in the polyolefin 101 starting material. "Soluble" as used to describe the bioavailable carbon product 108 refers to material that is dissolved in the liquid fraction of the reaction mixture. In some embodiments, the water solubility of the bioavailable carbon product 108 can be about 0.1 grams per 100 milliliters of water to about 30 g per 100 mL of water or about 0.1 g per 100 mL of water to about miscible.

The bioavailable carbon product 108 is a soluble organic material. The bioavailable carbon product 108 can contain organic compounds with one or more functional groups including a carboxylic acid, a hydroxyl group, a sulfonic acid group, and combinations thereof. Depending on the type of polyolefin 101 starting material, the bioavailable carbon product 108 can further include other types of functional groups. Examples of additional functional group types include amides, esters, ethers, alkenyl groups, aryl groups, and halogen groups. In some embodiments, the average molecular weight of the bioavailable carbon product 108 can be about 50 grams per mole (g/mol) to about 900 g/mol or about 100 g/mol to about 500 g/mol.

The bioavailable carbon product 108 can be used as a sole or supplemental carbon source for microbial growth. In some embodiments, the bioavailable carbon product 108 can be used as the sole carbon source in a growth medium. In some embodiments, the bioavailable carbon product 108 can be used directly as a carbon source for microbial growth without additional purification and/or isolation steps. Microbial strains that can grow in the presence of the bioavailable carbon product 108 as a carbon source include anaerobic and aerobic bacteria and fungi. Examples of suitable microbial strains include *Exophiala alcalophila, Corynebacterium glutamicum, Pseudomonas stutzeri, Pseudomonas putida, Rhodococcus jostii, Yarrowia lipolytica, Rhodococcus rhodochrous, Rhodococcus ruber, Streptomyces venezuelae, Pseudomonas* sp. Rh926, *Brevundimonas vesicularis, Sphingomonas* sp. PWE1, *Candida maltosa, Delftia acidovorans, Sphyingopyxis wiflariensis*, and *Cobetia marina.*

The insoluble material 109 can include zero wt % to 50 wt % of the carbon contained in the polyolefin 101 starting material. In some embodiments, the insoluble material 109 can include about 5 wt % to about 25 wt % of the carbon contained in the polyolefin 101 starting material. "Insoluble" as used to describe the insoluble material 109 refers to material that is not dissolved in the liquid fraction of the bond cleavage reaction mixture.

EXAMPLES

Example 1. Depolymerization of Low-Density Polyethylene (LDPE) Film

LDPE substrate (0.8 grams, 30 micrometers thickness film, Goodfellow) was combined with 20% fuming sulfuric acid (20 milliliters). The reaction mixture was heated to 50° C. and stirred for 1 hour (h). During the 1 h of stirring, the temperature increased to 50° C. from room temperature due to the exothermic reaction. After cooling to room temperature, the mixture was filtered, and the solids were rinsed with water to remove excess sulfuric acid. The sulfonated solids were dried (1.33 g). The sulfonated solids had a 17:1 carbon to sulfur molar ratio.

Then the sulfonated solids (1.18 grams, 0.607 g carbon) were combined with water at a concentration of 5 milligrams (mg) of solids per milliliter (mL) of water at a pH of 6. Iron sulfate was added to the mixture at a concentration of 0.2 millimolar (mM, 0.02 iron to sulfur molar ratio). Hydrogen peroxide was added in two increments for a total concentration of 0.5% in the reaction mixture (1.4 $H_2O_2$ to monomer molar ratio). The reaction mixture was heated to 50° C. and allowed to proceed until the $H_2O_2$ fully dissipated. The mixture was filtered to provide insoluble solids (0.17 g) and a filtrate of soluble materials. The filtrate was concentrated to yield 1.04 g of solids. The total dissolved organic carbon was 0.126 g.

Example 2. Depolymerization of Low-Density Polyethylene (LDPE) Film

LDPE substrate (0.5 grams, 30 micrometers thickness film, Goodfellow) was combined with 15% fuming sulfuric acid (20 milliliters). The reaction mixture was stirred at 50° C. for 1.0 h. The mixture was filtered, and the solids were rinsed with water to remove excess sulfuric acid. The sulfonated solids were dried (1.22 g). The sulfonated solids had a 5:1 carbon to sulfur molar ratio.

Then the sulfonated solids (0.593 grams, 0.186 g of carbon) were combined with water at a concentration of 10 milligrams of solids per milliliter of water at a pH of 6. Iron sulfate was added to the mixture at a concentration of 1 mM (0.02 iron to sulfur molar ratio). Hydrogen peroxide was added in three increments for a total concentration of 0.75% in the reaction mixture (1.7 $H_2O_2$ to monomer molar ratio). The reaction mixture was heated to 50° C. and allowed to proceed until the $H_2O_2$ fully dissipated. The mixture was filtered to provide insoluble solids (0.17 g) and a filtrate of soluble materials. The filtrate was concentrated to yield 0.625 grams (g) of solids. The total dissolved organic carbon was 0.083 g.

Example 3. Depolymerization of Low-Density Polyethylene (LDPE) Film

LDPE substrate (0.5 grams, 30 micrometers thickness film, Goodfellow) was combined with 15% fuming sulfuric acid (20 milliliters). The reaction mixture was stirred at 50° C. for 1.0 h. The mixture was filtered, and the solids were rinsed with water to remove excess sulfuric acid. The sulfonated solids were dried (1.22 g). The sulfonated solids had a 5:1 carbon to sulfur molar ratio.

The sulfonated solids (0.593 g) were added to an aqueous solution of $FeSO_4$-$7H_2O$ (1.83 g in 30 mL water; 0.3 iron to sulfur molar ratio). After stirring overnight, the sulfonated solid material was removed, washed with water, and dried (0.641 g). A weight gain of 0.048 g resulted from iron that was bound to the sulfonated solid material (iron-loaded sulfonated solids). The iron-loaded sulfonated solids (0.500 g, 0.137 g of carbon) were combined with water at a concentration of 10 milligrams of solids per milliliter of water at a pH of 6. Hydrogen peroxide was added in two increments for a total concentration of 1.0% in the reaction mixture ($H_2O_2$ to monomer molar ratio of 2.6). The reaction mixture was heated to 50° C. and allowed to proceed until the $H_2O_2$ fully dissipated. The mixture was filtered to provide insoluble solids (0.020 g) and a filtrate of soluble materials. The filtrate was concentrated to yield 0.524 g of solids (70 mg of carbon).

Table 1 provides a side-by-side comparison of the reaction conditions for Examples 1 to 3 along with the calculated carbon component percentages based on mass recovery and elemental analysis of the reaction products.

TABLE 1

| Example | 1 | 2 | 3 |
|---|---|---|---|
| C/S ratio | 17 | 5 | 5 |
| Fe/S ratio | 0.02 | 0.02 | 0.3 |
| $H_2O_2$/monomer ratio | 1.4 | 1.7 | 2.6 |
| Sulfonation C loss (%) | 0 | 10 | 10 |
| Bond cleavage soluble C recovery (%) [carbon in bioavailable carbon product 108] | 21 | 45 | 51 |
| Bond cleavage insoluble C recovery (%) [carbon in insoluble material 109] | 21 | 6 | 10 |
| Bond cleavage C loss (%) [carbon in volatile compounds 110] | 58 | 49 | 39 |

Figure 2:
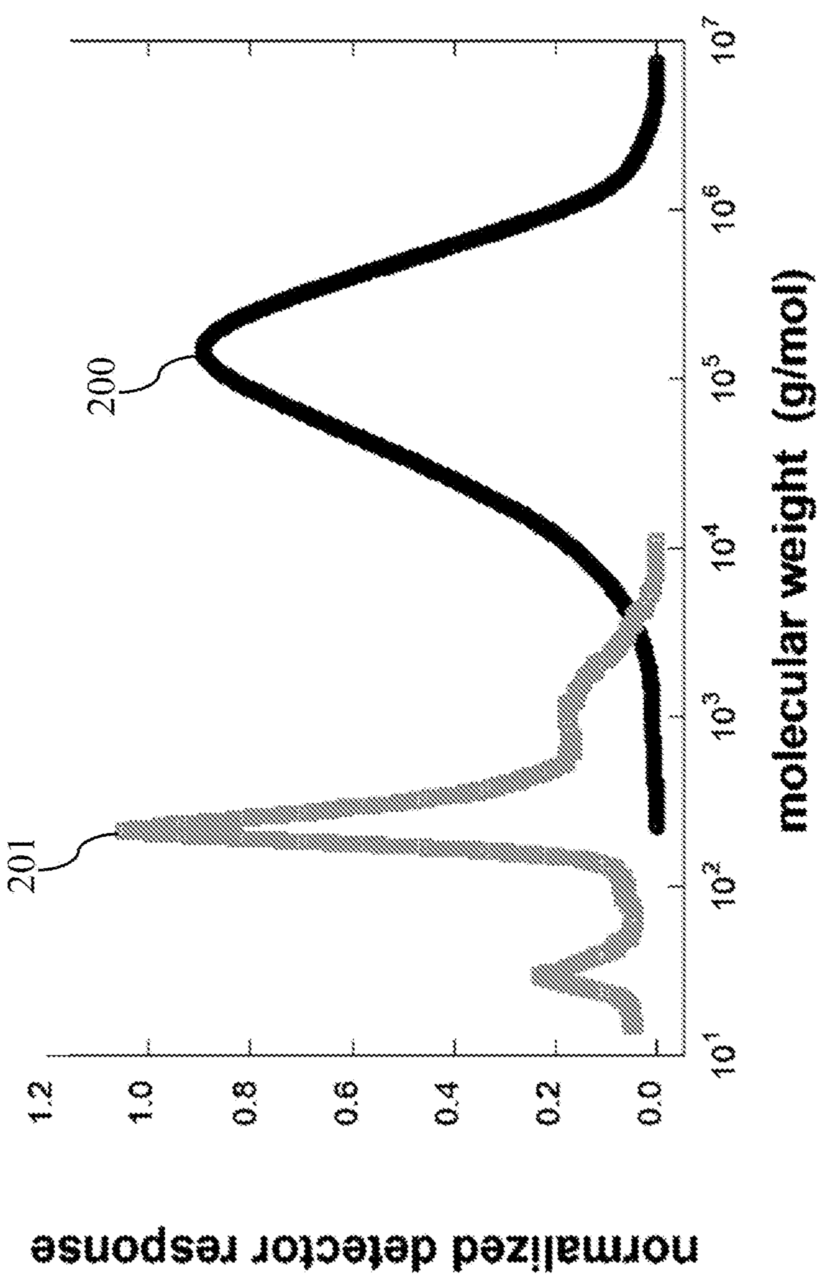
FIG. 2 is a graph illustrating normalized detector response versus molecular weight in grams per mole in accordance with Example 1.

The depolymerized substrate of Example 1 was analyzed by size exclusion chromatography (using an Agilent 1260 HPLC system with PL Aquagel-PH30 and PL Aquagel-OH50 columns in series at 30° C. with 1 mM ammonium bicarbonate buffer at pH 9 as eluant and using polystyrene sulfonate standards for calibration) and a peak molecular weight of about 220 g/mol was measured (peak 201 as labeled in FIG. 2). In comparison, the LDPE substrate was analyzed by SEC (using three Agilent PLgel Olexis columns with trichlorobenzene as eluant at 135° C. and using polystyrene standards for calibration) and had a peak molecular weight of about 154,000 g/mol (peak 200 as labeled in FIG. 2). The depolymerized substrate of Examples 2 and 3 were also analyzed by size exclusion chromatography and exhibited a peak molecular weight of about 220 g/mol (data not shown).

Figure 3:
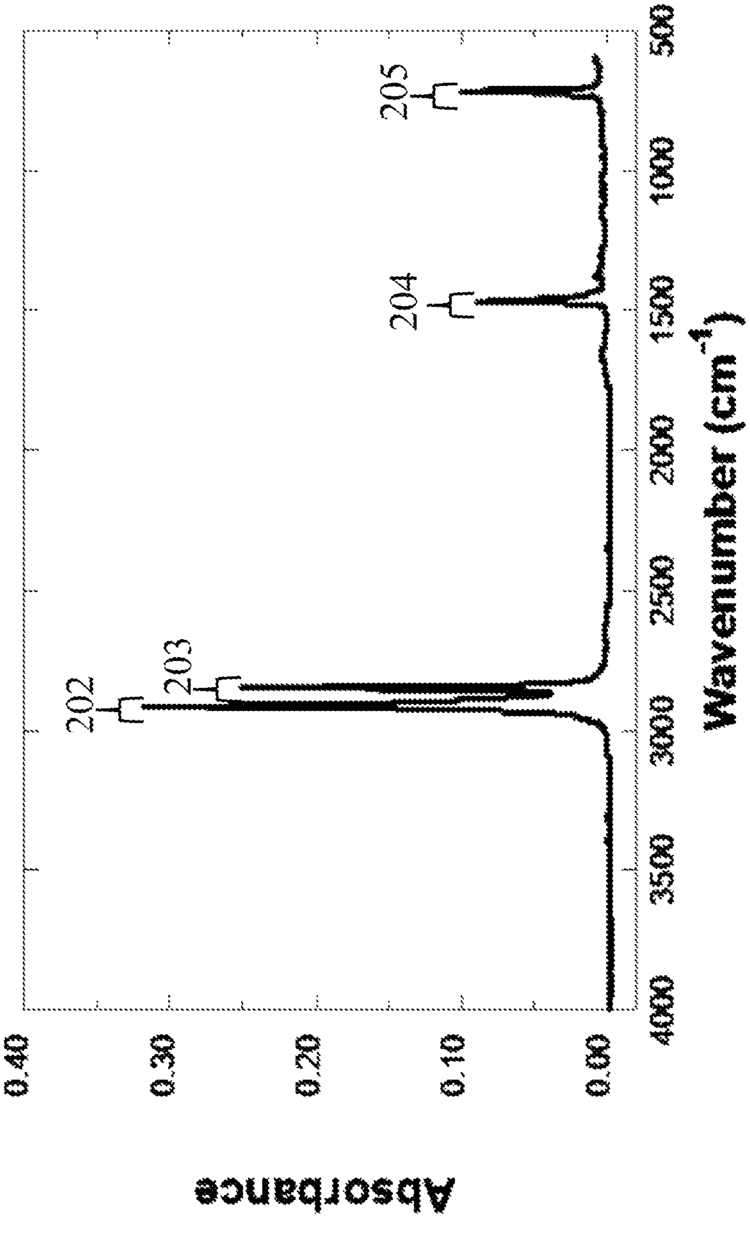
FIG. 3 is a graph illustrating infrared absorbance in relative units versus wavenumbers in inverse centimeters for low density polyethylene.

The annotated FTIR spectrum of the LDPE substrate of Examples 1 to 3, as shown in FIG. 3, illustrates asymmetric C—H stretching (peak 202), symmetric C—H stretching (peak 203), $CH_3$ pending (peak 204), and $CH_2$ rocking (peak 205).

Figure 4:
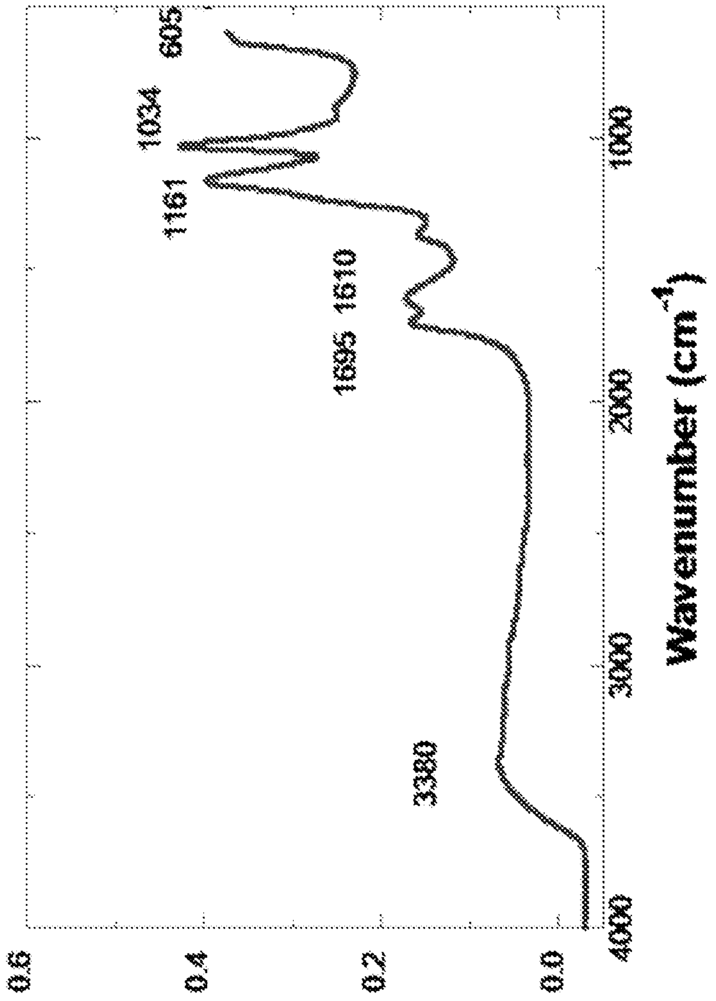
FIG. 4 is a graph illustrating infrared absorbance in relative units versus wavenumbers in inverse centimeters for a sulfonated solids sample in accordance with Example 1.

A representative annotated FTIR spectrum of the sulfonated solids as described in Example 1 is shown in FIG. 4. As shown in the spectrum, a peak at 3380 wavenumbers ($cm^{-1}$) indicates OH stretching, peaks at 1695 $cm^{-1}$ and 1610 $cm^{-1}$ indicate C═C stretching, a peak at 1161 $cm^{-1}$ indicates asymmetrical —$SO_3$ bond stretching, a peak at 1034 $cm^{-1}$ indicates symmetrical —$SO_3$ bond stretching, and a peak at 605 $cm^{-1}$ was attributed to C—S stretching.

Figure 5:
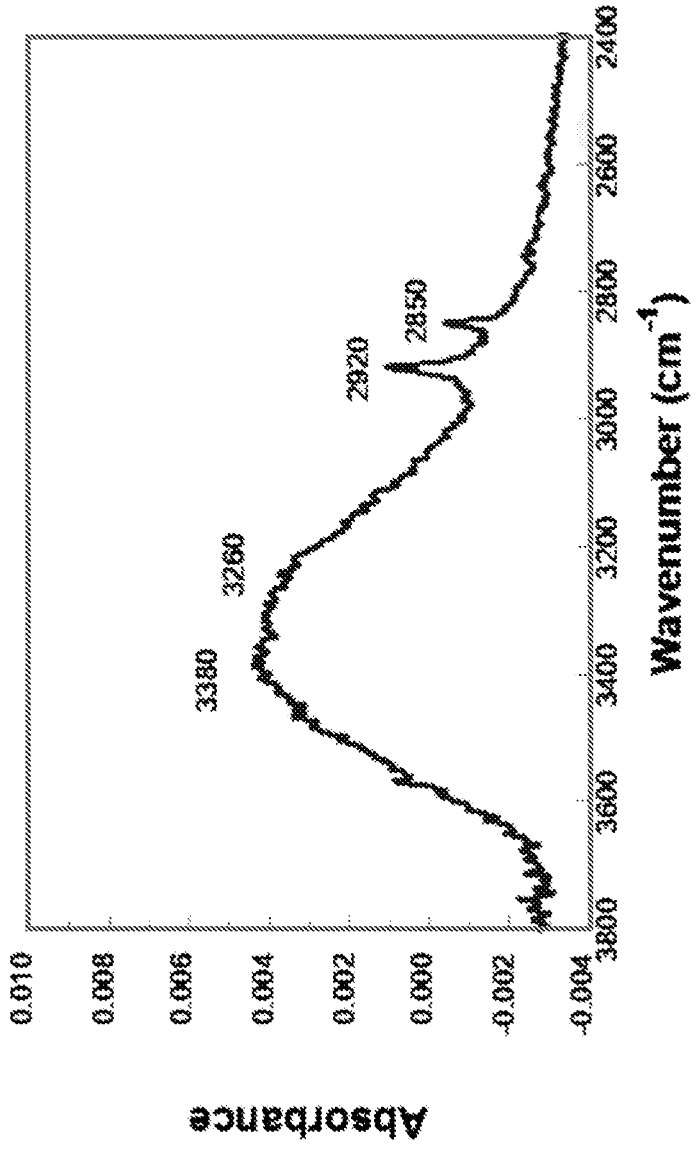
FIG. 5 is a graph illustrating infrared absorbance in relative units versus wavenumbers in inverse centimeters for the soluble depolymerized filtrate in accordance with Example 1.
Figure 6:
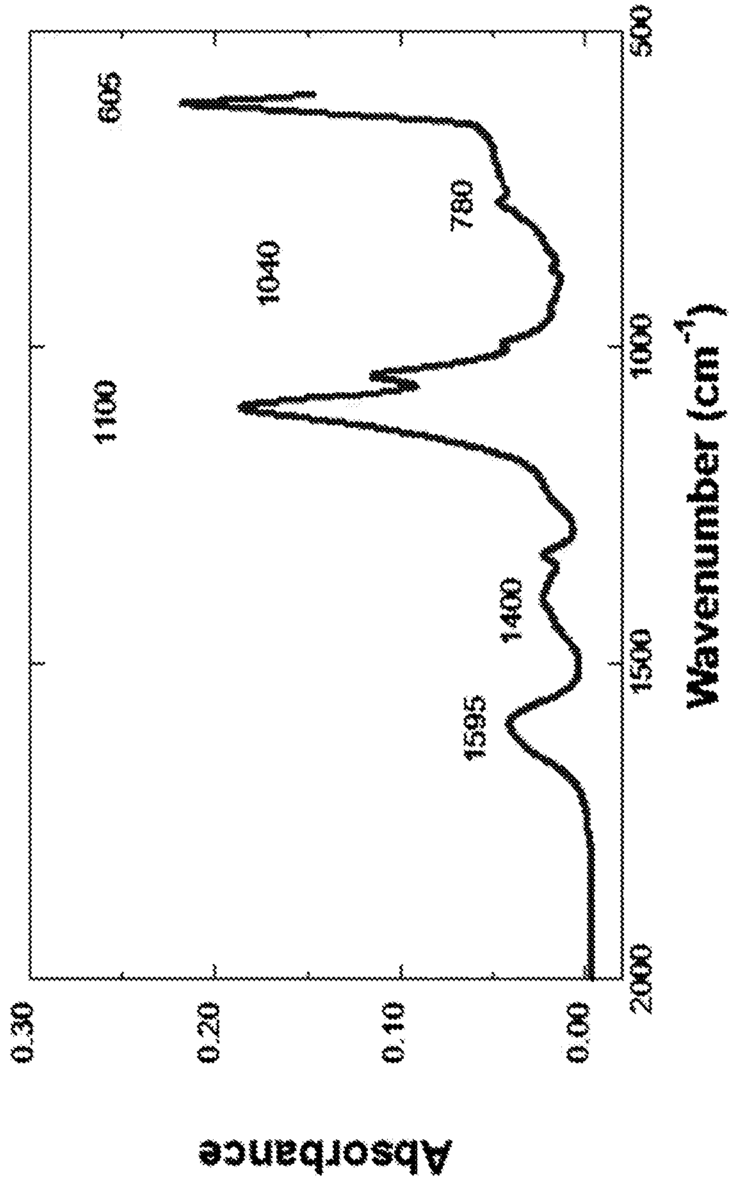
FIG. 6 is a graph illustrating infrared absorbance in relative units versus wavenumbers in inverse centimeters for the soluble depolymerized filtrate in accordance with Example 1.

Representative annotated FTIR spectra of the soluble depolymerized filtrate as described in Example 1 is shown in FIG. 5 (wavenumber range 2400 $cm^{-1}$ to 3800 cm 1) and FIG. 6 (wavenumber range 500 $cm^{-1}$ to 2000 $cm^{-1}$). As shown in FIG. 5, peaks at 3380 $cm^{-1}$ and 3260 $cm^{-1}$ indicate OH stretching and peaks at 2920 $cm^{-1}$ and 2850 $cm^{-1}$ indicate C—H bone stretching. As shown in FIG. 6, a peak 1595 $cm^{-1}$ indicates asymmetrical carboxylate stretching, a peak at 1400 $cm^{-1}$ indicates symmetrical carboxylate stretching, a peak at 1100 $cm^{-1}$ indicates the alkoxy C—O stretch of primary, secondary, and tertiary alcohols and along with asymmetrical-$SO_3$ stretching, a peak at 1040 indicates symmetrical-$SO_3$ stretching, and a peak 605 $cm^{-1}$ was attributed to C—S stretching.

Example 4. Depolymerization of Low-Density Polyethylene (LDPE) Film

LDPE substrate (3 g, 30 micrometers thickness film, Goodfellow) was combined with 120 mL of 20% fuming sulfuric acid. The reaction mixture was initially heated to 40° C. and then allowed to cool to room temperature. The reaction mixture was stirred at room temperature for 1.5 h. The mixture was filtered, and the solids were rinsed with water to remove excess sulfuric acid. The sulfonated solids were dried (7.78 g). The carbon to sulfur molar ratio was 4:1.

The sulfonated solids (7 g) were added to an aqueous solution of $FeSO_4$-$7H_2O$ (2 g in 50 mL water). After stirring overnight, the solid were removed, washed with water, and dried (7.47 g) to provide a weight gain of 0.47 g from iron loading on the sulfonated polyolefin (iron-loaded sulfonated solids). The iron-loaded sulfonated solids (7 g) were added to water at a concentration of 10 milligrams of solids per milliliter of water at a pH of 6. Hydrogen peroxide was added in two increments for a total concentration of 1.5% in the reaction mixture. The mixture was filtered to provide insoluble solids (0.02 g) and a filtrate of soluble materials. The carbon component percentages for the sulfonation and bond cleavage steps based on mass recovery and elemental analysis of the reaction products are given in Table 2.

Example 5. Depolymerization of Low-Density Polyethylene (LDPE) Film

LDPE substrate (0.3 g, 30 micrometers thickness film, Goodfellow) was combined with 120 mL of 1.5% fuming sulfuric acid. The reaction mixture was initially heated to 40° C. and then allowed to cool to room temperature. The reaction mixture was stirred at room temperature for 1.5 h. The mixture was filtered, and the solids were rinsed with water to remove excess sulfuric acid. The sulfonated solids were dried (7.33 g). The carbon to sulfur (C/S) mole ratio was 4.8:1 for the sulfonated solids.

The sulfonated solids (7.00 g) were added to an aqueous solution of $FeSO_4$-$7H_2O$ (2 g in 50 mL water). After stirring overnight, the sulfonated solid material was removed, washed with water, and dried (7.44 g) to provide a weight gain of 0.44 g from iron loading on the sulfonated polyolefin (iron-loaded sulfonated solids). Then the iron-loaded sulfonated solids (7 g) were combined with water at a concentration of 10 milligrams of solids per milliliter of water at a pH of 6. Hydrogen peroxide was added in two increments for a total concentration of 1.5% in the reaction mixture. The mixture was filtered to provide insoluble solids (0.02 g) and a filtrate of soluble materials. The carbon component percentages for the sulfonation and bond cleavage steps based on mass recovery and elemental analysis of the reaction products are given in Table 2.

Example 6. Depolymerization of Low-Density Polyethylene (LDPE) Film

LDPE substrate (3 g, 30 micrometers thickness film, Goodfellow) was combined with 120 mL of 12.5% fuming sulfuric acid. The reaction mixture was initially heated to 60° C. and then allowed to cool to room temperature. The reaction mixture was then stirred at room temperature for 1.5 h. The mixture was filtered, and the sulfonated solids were rinsed with water to remove excess sulfuric acid and dried (4.49 g). The carbon to sulfur molar ratio was 16:1 for the sulfonated solids.

The sulfonated solids (3 g) were added to an aqueous solution of $FeSO_4$-$7H_2O$ (2 g in 50 mL water). After stirring overnight, the sulfonated solid material was removed, washed with water, and dried (3.12 g) to provide a weight gain of 0.12 g from iron loading on the sulfonated polyolefin (iron-loaded sulfonated solids). Then the iron-loaded sulfonated solids (3 g) were combined with water at a concentration of 10 milligrams of solids per milliliter of water at a pH of 6. Hydrogen peroxide was added in two increments for a total concentration of 1.5% in the reaction mixture. The mixture was filtered to provide insoluble solids (0.6 g) and a filtrate of soluble materials.

The carbon component percentages for the sulfonation and bond cleavage steps based on elemental analysis and total organic carbon measurements of the reaction products are given in Table 2.

Table 2 provides a side-by-side comparison of the reaction conditions for Examples 4 to 6 along with the calculated carbon component percentages for the sulfonation and bond cleavage steps based on mass recovery and elemental analysis of the reaction products.

TABLE 2

| Example | 4 | 5 | 6 |
|---|---|---|---|
| C/S ratio | 4 | 4.8 | 16 |
| Sulfonation C loss (%) | 3.9 | 7.2 | 6.5 |
| Bond cleavage soluble C recovery (%) [carbon in bioavailable carbon product 108] | 49 | 60 | 13 |

Example 7. Liquid Chromatography Mass Spectrometry (LC-MS) of Depolymerized PE The soluble depolymerized filtrate prepared as described in Example 1 was subjected to liquid chromatography for two different column conditions: Hydrophilic Interaction (HILIC Column) and a C18 column. The detected mass to charge ratios (m/z) are provided in Table 3. The molecular weights are listed in order from highest abundance to lowest abundance.

TABLE 3

LC-MS Molecular Weight Distribution for Depolymerized PE

| HILIC column (g/mol) | | | | C18 column (g/mol) | | | |
|---|---|---|---|---|---|---|---|
| No. | g/mol | No. | g/mol | No. | g/mol | No. | g/mol |
| 1 | 196.97 | 25 | 187.02 | 1 | 138.97 | 26 | 250.98 |
| 2 | 202.94 | 26 | 185.89 | 2 | 196.98 | 27 | 296.93 |
| 3 | 94.985 | 27 | 268.99 | 3 | 195 | 28 | 220.97 |
| 4 | 384.92 | 28 | 238.98 | 4 | 94.987 | 29 | 151.98 |
| 5 | 452.91 | 29 | 176.98 | 5 | 140.98 | 30 | 266.98 |
| 6 | 152.99 | 30 | 135.03 | 6 | 218.96 | 31 | 237.01 |
| 7 | 174.95 | 31 | 170.99 | 7 | 160.96 | 32 | 189 |
| 8 | 122.98 | 32 | 470.78 | 8 | 222.99 | 33 | 310.93 |
| 9 | 222.99 | 33 | 390.88 | 9 | 122.98 | 34 | 264.95 |
| 10 | 117.02 | 34 | 193.01 | 10 | 117.02 | 35 | 345.92 |
| 11 | 143.92 | 35 | 302.88 | 11 | 226.98 | 36 | 241 |
| 12 | 187.9 | 36 | 294.95 | 12 | 198.98 | 37 | 234.98 |
| 13 | 226.97 | 37 | 211.99 | 13 | 228.94 | 38 | 144.97 |
| 14 | 139.97 | 38 | 80.97 | 14 | 254.98 | 39 | 231.01 |
| 15 | 181.07 | 39 | 151.99 | 15 | 280.9 | 40 | 234.95 |
| 16 | 198.97 | 40 | 167 | 16 | 197.98 | 41 | 143.98 |
| 17 | 197.98 | 41 | 189 | 17 | 302.88 | 42 | 154.01 |
| 18 | 254.98 | 42 | 196 | 18 | 138.01 | 43 | 326.9 |
| 19 | 216.95 | 43 | 220.94 | 19 | 80.972 | 44 | 185 |
| 20 | 402.79 | 44 | 362.93 | 20 | 139.98 | 45 | 165.98 |
| 21 | 139.1 | 45 | 197.05 | 21 | 238.98 | 46 | 290.95 |
| 22 | 331.83 | 46 | 241 | 22 | 268.99 | 47 | 262.98 |
| 23 | 189.91 | 47 | 286.94 | 23 | 170.99 | 48 | 203.02 |
| 24 | 222.95 | 48 | 317.94 | 24 | 286.94 | 49 | 281.88 |
| | | 49 | 203.01 | 25 | 157.99 | 50 | 229.99 |
| | | | | | | 51 | 274.98 |

Selected chemical structures consistent with the detected m/z are illustrated below with the chemical formula and exact mass for each compound (assuming z=1). The structures are grouped into families with m/z that vary by m/z corresponding to a —$CH_2$— unit.

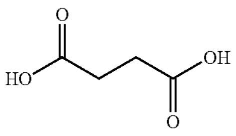

Chemical Formula: $C_4H_6O_3$
Exact Mass: 118.03

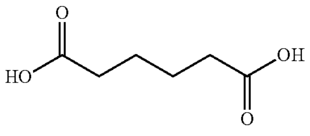

Chemical Formula: $C_6H_{10}O_4$
Exact Mass: 146.06

-continued

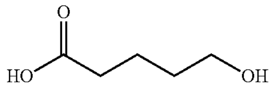

Chemical Formula: $C_5H_{10}O_3$
Exact Mass: 118.06

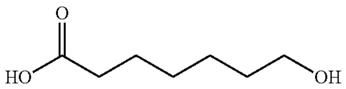

Chemical Formula: $C_7H_{14}O_3$
Exact Mass: 146.09

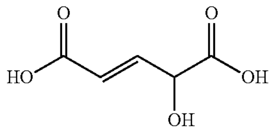

Chemical Formula: $C_5H_6O_3$
Exact Mass: 146.02

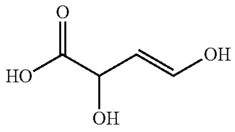

Chemical Formula: $C_4H_6O_3$
Exact Mass: 118.03

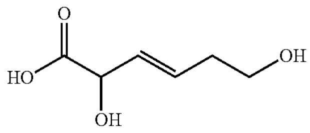

Chemical Formula: $C_6H_{10}O_4$
Exact Mass: 146.06

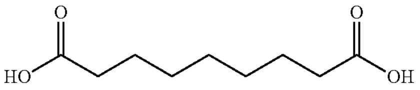

Chemical Formula: $C_9H_{16}O_4$
Exact Mass: 188.10

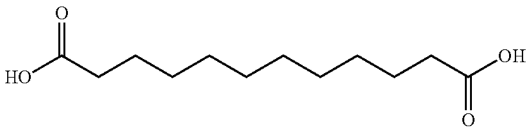

Chemical Formula: $C_{12}H_{22}O_4$
Exact Mass: 230.15

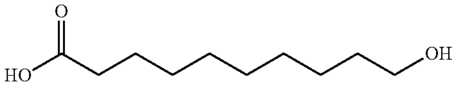

Chemical Formula: $C_{10}H_{20}O_3$
Exact Mass: 188.14

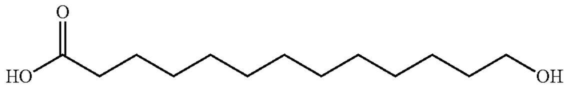

Chemical Formula: $C_{13}H_{26}O_3$
Exact Mass: 230.19

-continued

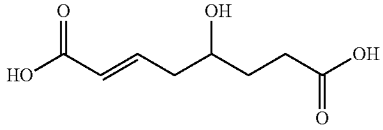

Chemical Formula: $C_8H_{12}O_5$
Exact Mass: 188.07

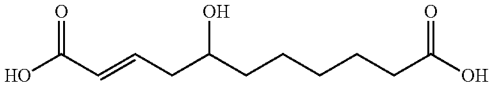

Chemical Formula: $C_{11}H_{18}O_5$
Exact Mass: 230.12

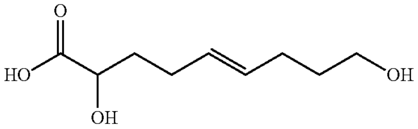

Chemical Formula: $C_9H_{16}O_4$
Exact Mass: 188.10

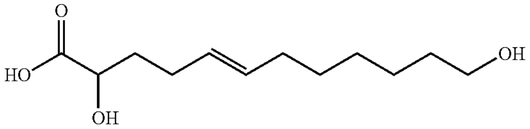

Chemical Formula: $C_{12}H_{22}O_4$
Exact Mass: 230.15

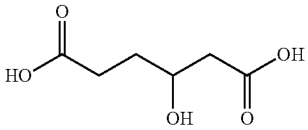

Chemical Formula: $C_6H_{10}O_5$
Exact Mass: 162.05

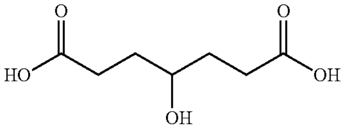

Chemical Formula: $C_7H_{12}O_3$
Exact Mass: 176.07

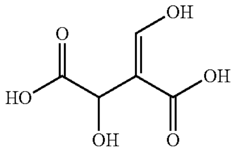

Chemical Formula: $C_5H_6O_6$
Exact Mass: 162.02

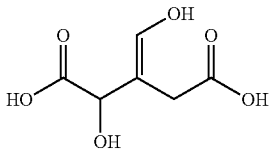

Chemical Formula: $C_6H_8O_6$
Exact Mass: 176.03

-continued

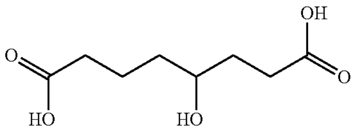

Chemical Formula: $C_8H_{14}O_5$
Exact Mass: 190.08

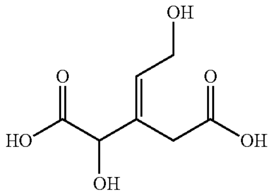

Chemical Formula: $C_7H_{10}O_6$
Exact Mass: 190.05

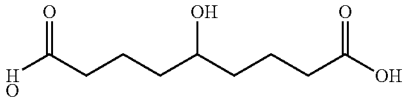

Chemical Formula: $C_9H_{16}O_5$
Exact Mass: 204.10

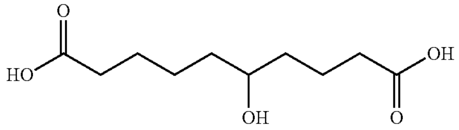

Chemical Formula: $C_{10}H_{18}O_5$
Exact Mass: 218.12

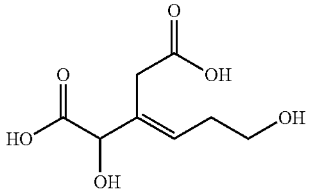

Chemical Formula: $C_8H_{12}O_6$
Exact Mass: 204.06

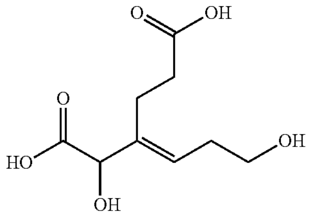

Chemical Formula: $C_9H_{14}O_6$
Exact Mass: 218.08

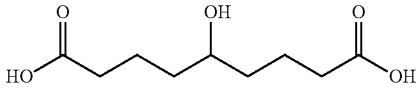

Chemical Formula: $C_{11}H_{20}O_5$
Exact Mass: 232.13

-continued

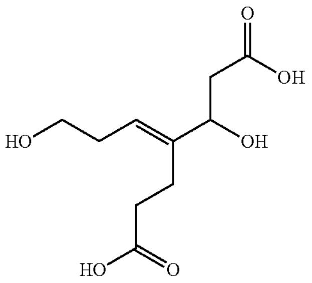

Chemical Formula: $C_{10}H_{16}O_6$
Exact Mass: 232.09

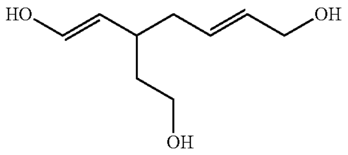

Chemical Formula: $C_9H_{16}O_3$
Exact Mass: 172.11

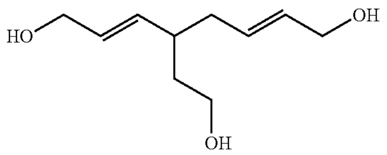

Chemical Formula: $C_{10}H_{18}O_3$
Exact Mass: 186.13

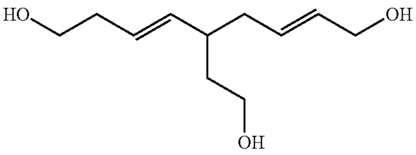

Chemical Formula: $C_{11}H_{20}O_3$
Exact Mass: 200.14

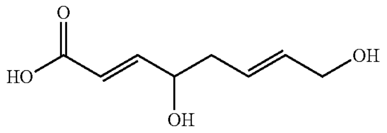

Chemical Formula: $C_8H_{12}O_4$
Exact Mass: 172.07

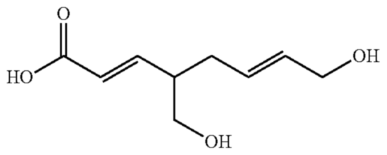

Chemical Formula: $C_9H_{14}O_4$
Exact Mass: 186.09

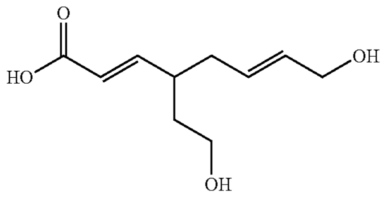

Chemical Formula: $C_{10}H_{16}O_4$
Exact Mass: 200.10

-continued

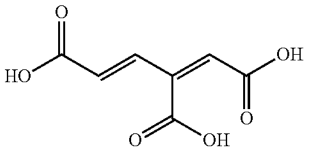

Chemical Formula: $C_7H_6O_6$
Exact Mass: 186.02

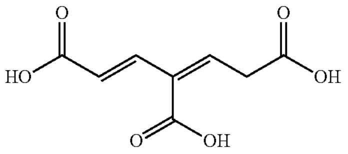

Chemical Formula: $C_8H_8O_6$
Exact Mass: 200.03

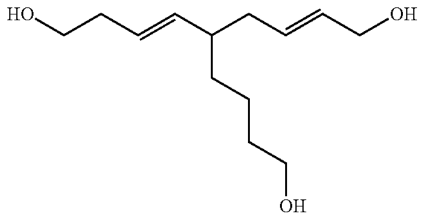

Chemical Formula: $C_{13}H_{24}O_3$
Exact Mass: 228.17

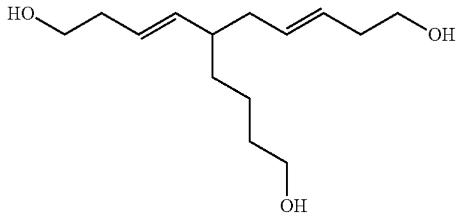

Chemical Formula: $C_{14}H_{26}O_3$
Exact Mass: 242.19

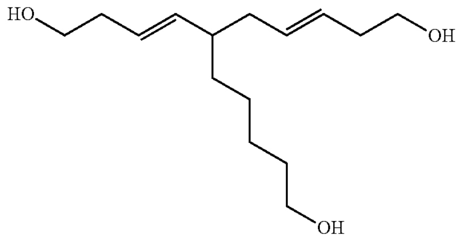

Chemical Formula: $C_{15}H_{26}O_3$
Exact Mass: 256.20

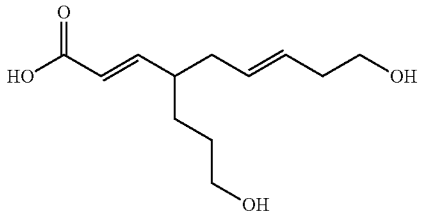

Chemical Formula: $C_{12}H_{20}O_4$
Exact Mass: 228.14

-continued

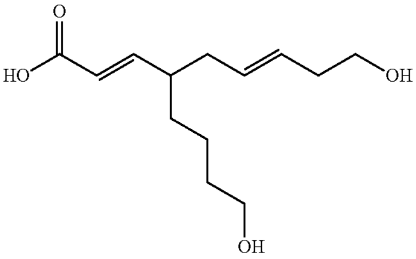

Chemical Formula: $C_{13}H_{22}O_4$
Exact Mass: 242.15

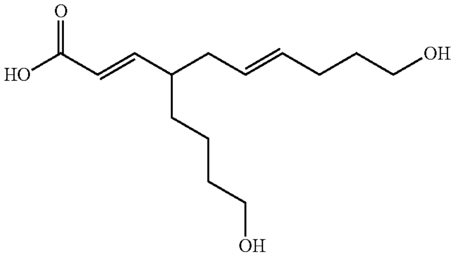

Chemical Formula: $C_{14}H_{24}O_4$
Exact Mass: 256.17

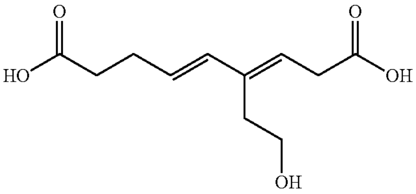

Chemical Formula: $C_{11}H_{16}O_5$
Exact Mass: 228.10

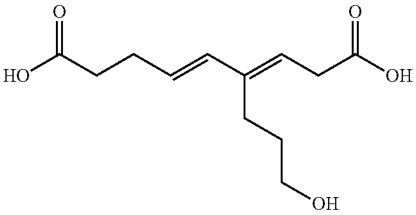

Chemical Formula: $C_{12}H_{18}O_5$
Exact Mass: 242.12

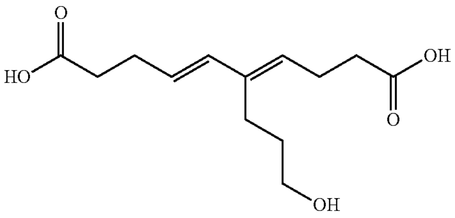

Chemical Formula: $C_{13}H_{20}O_5$
Exact Mass: 256.13

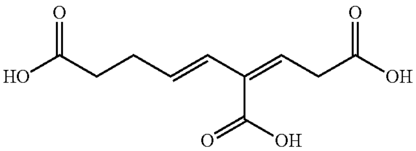

Chemical Formula: $C_{10}H_{12}O_6$
Exact Mass: 228.06

-continued

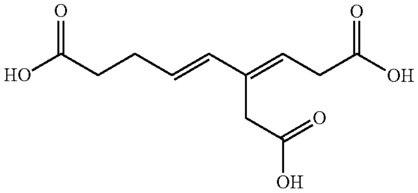

Chemical Formula: $C_{11}H_{14}O_6$
Exact Mass: 242.08

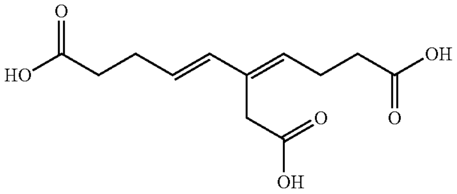

Chemical Formula: $C_{12}H_{16}O_6$
Exact Mass: 256.09

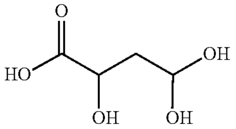

Chemical Formula: $C_4H_8O_5$
Exact Mass: 136.04

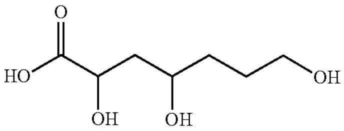

Chemical Formula: $C_7H_{14}O_5$
Exact Mass: 178.08

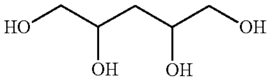

Chemical Formula: $C_5H_{12}O_4$
Exact Mass: 136.07

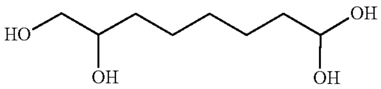

Chemical Formula: $C_8H_{18}O_4$
Exact Mass: 178.12

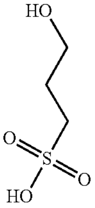

Chemical Formula: $C_3H_8O_4S$
Exact Mass: 140.01

-continued
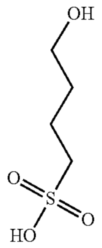
Chemical Formula: $C_4H_{10}O_4S$
Exact Mass: 154.03
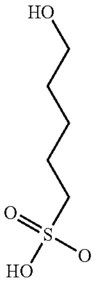
Chemical Formula: $C_5H_{12}O_4S$
Exact Mass: 168.05
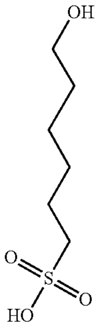
Chemical Formula: $C_6H_{14}O_4S$
Exact Mass: 182.06
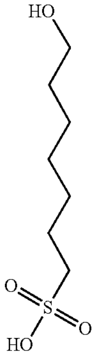
Chemical Formula: $C_7H_{16}O_4S$
Exact Mass: 196.08
-continued
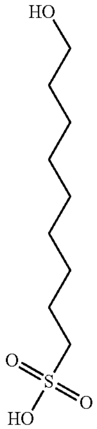
Chemical Formula: $C_9H_{20}O_4S$
Exact Mass: 224.11
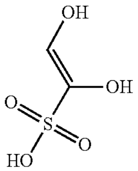
Chemical Formula: $C_2H_4O_5S$
Exact Mass: 139.98
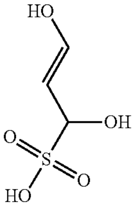
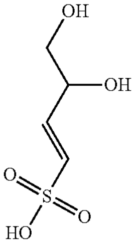
Chemical Formula: $C_4H_8O_5S$
Exact Mass: 168.01
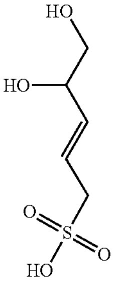
Chemical Formula: $C_5H_{10}O_5S$
Exact Mass: 182.02

-continued

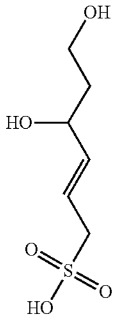

Chemical Formula: $C_6H_{12}O_5S$
Exact Mass: 196.04

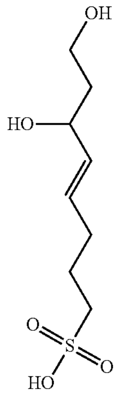

Chemical Formula: $C_8H_{16}O_5S$
Exact Mass: 224.07

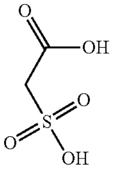

Chemical Formula: $C_2H_4O_5S$
Exact Mass: 139.98

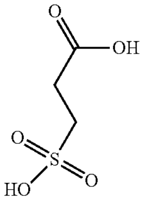

Chemical Formula: $C_3H_6O_5S$
Exact Mass: 153.99

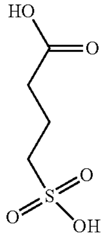

Chemical Formula: $C_4H_8O_5S$
Exact Mass: 168.01

-continued

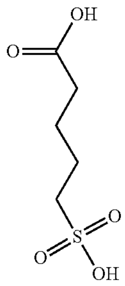

Chemical Formula: $C_5H_{10}O_5S$
Exact Mass: 182.02

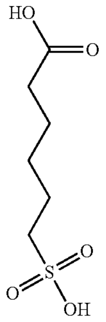

Chemical Formula: $C_6H_{12}O_5S$
Exact Mass: 196.04

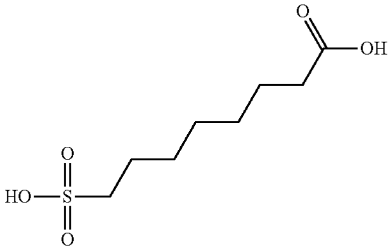

Chemical Formula: $C_8H_{16}O_5S$
Exact Mass: 224.07

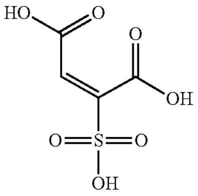

Chemical Formula: $C_4H_4O_7S$
Exact Mass: 195.97

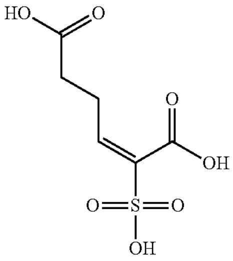

Chemical Formula: $C_6H_8O_7S$
Exact Mass: 224.00

-continued

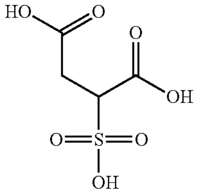

Chemical Formula: $C_4H_6O_7S$
Exact Mass: 197.98

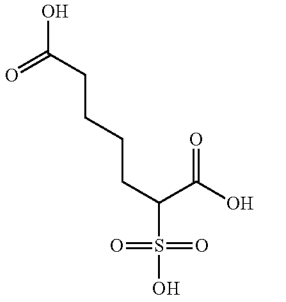

Chemical Formula: $C_7H_{12}O_7S$
Exact Mass: 240.03

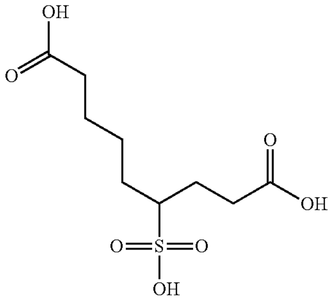

Chemical Formula: $C_9H_{16}O_7S$
Exact Mass: 268.06

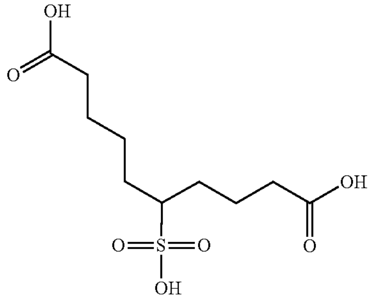

Chemical Formula: $C_{10}H_{18}O_7S$
Exact Mass: 282.08

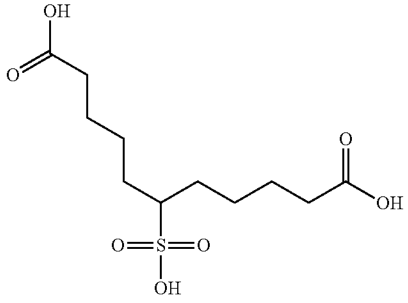

Chemical Formula: $C_{11}H_{20}O_7S$
Exact Mass: 296.09

-continued

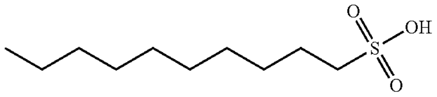

Chemical Formula: $C_{10}H_{22}O_3S$
Exact Mass: 222.13

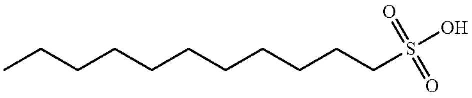

Chemical Formula: $C_{11}H_{24}O_3S$
Exact Mass: 236.14

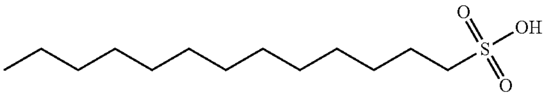

Chemical Formula: $C_{13}H_{28}O_3S$
Exact Mass: 264.18

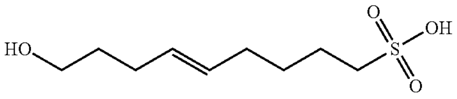

Chemical Formula: $C_9H_{18}O_4S$
Exact Mass: 222.09

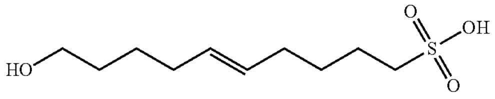

Chemical Formula: $C_{10}H_{20}O_4S$
Exact Mass: 236.11

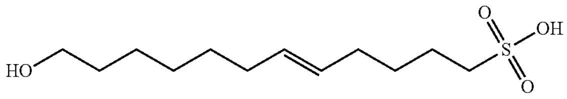

Chemical Formula: $C_{12}H_{24}O_4S$
Exact Mass: 264.14

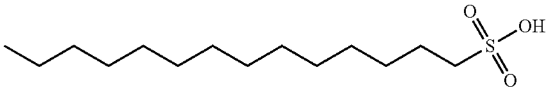

Chemical Formula: $C_{14}H_{30}O_3S$
Exact Mass: 278.19

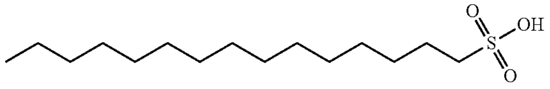

Chemical Formula: $C_{15}H_{32}O_3S$
Exact Mass: 292.21

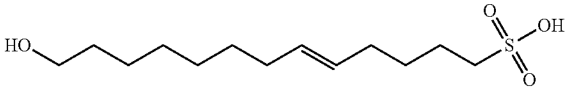

Chemical Formula: $C_{13}H_{26}O_4S$
Exact Mass: 278.6

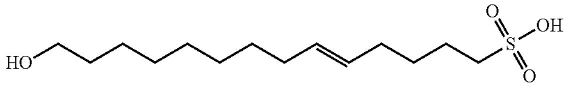

Chemical Formula: $C_{14}H_{28}O_4S$
Exact Mass: 292.17

-continued

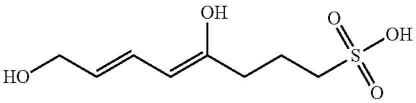

Chemical Formula: $C_8H_{14}O_5S$
Exact Mass: 222.06

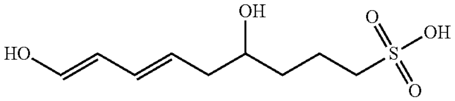

Chemical Formula: $C_9H_{16}O_5S$
Exact Mass: 236.07

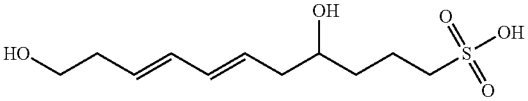

Chemical Formula: $C_{11}H_{20}O_5S$
Exact Mass: 264.10

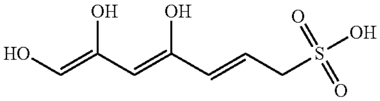

Chemical Formula: $C_7H_{10}O_6S$
Exact Mass: 222.02

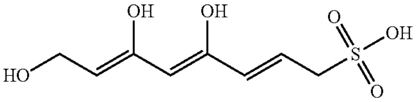

Chemical Formula: $C_8H_{12}O_6S$
Exact Mass: 236.04

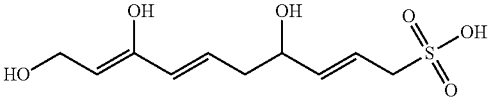

Chemical Formula: $C_{10}H_{16}O_6S$
Exact Mass: 264.07

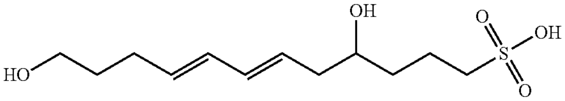

Chemical Formula: $C_{12}H_{22}O_5S$
Exact Mass: 278.12

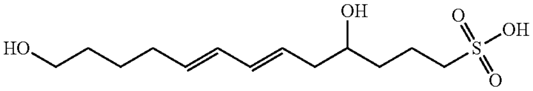

Chemical Formula: $C_{13}H_{24}O_5S$
Exact Mass: 292.13

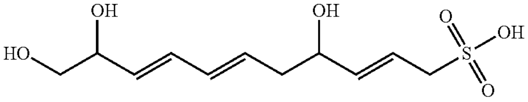

Chemical Formula: $C_{11}H_{18}O_6S$
Exact Mass: 278.08

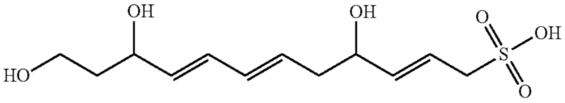

Chemical Formula: $C_{12}H_{20}O_6S$
Exact Mass: 292.10

-continued

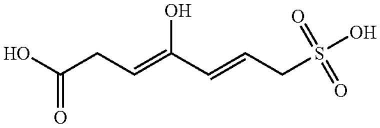

Chemical Formula: $C_7H_{10}O_6S$
Exact Mass: 222.02

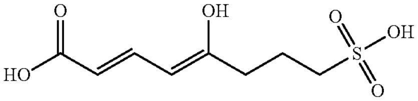

Chemical Formula: $C_8H_{12}O_6S$
Exact Mass: 236.04

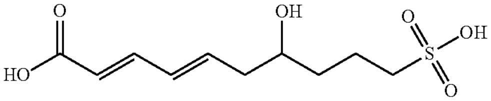

Chemical Formula: $C_{10}H_{16}O_6S$
Exact Mass: 264.07

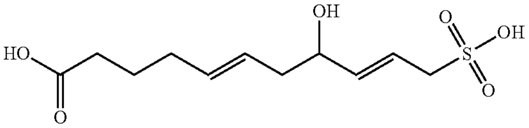

Chemical Formula: $C_{11}H_{18}O_6S$
Exact Mass: 278.08

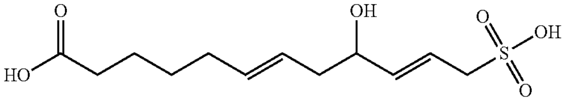

Chemical Formula: $C_{12}H_{20}O_6S$
Exact Mass: 292.10

Chemical Formula: $H_2O_3S$
Exact Mass: 81.97

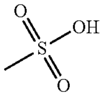

Chemical Formula: $CH_4O_3S$
Exact Mass: 95.99

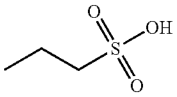

Chemical Formula: $C_3H_8O_3S$
Exact Mass: 124.02

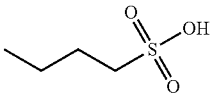

Chemical Formula: $C_4H_{10}O_3S$
Exact Mass: 138.04

-continued

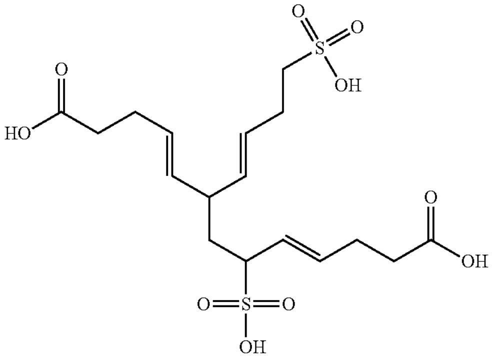

Chemical Formula: $C_{17}H_{26}O_{10}S_2$
Exact Mass: 454.10

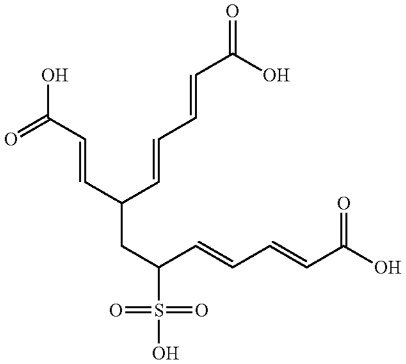

Chemical Formula: $C_{16}H_{18}O_9S$
Exact Mass: 386.07

Example 8. Biological Availability of Depolymerized LDPE as a Sole Carbon Source The depolymerized substrate from Example 1 was diluted into a minimal medium at a concentration of 0.5 milligrams per milliliter (mg/mL). The minimal medium contained the following components per liter: 0.05 g yeast extract, 0.5 g $KH_2PO_4$, 0.5 g $K_2HPO_4$, 2.5 g $(NH_4)_2SO_4$, 0.1 g NaCl, 0.01 g $FeSO_4$-$7H_2O$, 0.004 g $MnSO_4$—$H_2O$, 0.6 g $MgSO_4$-$7H_2O$, 0.02 g $CaCl_2$-$2H_2O$, 0.0002 g biotin, 0.0002 g thiamine. The pH was 3.8. The samples were then individually inoculated with a monoculture of one of the microbial strains listed in Table 4.

TABLE 4

Microbial Strains Tested in Labeled Order

| Sample ID | Microbial Strain |
|---|---|
| 1 | *Exophiala alcalophila* |
| 2 | *Bacillus subtilis* |
| 3 | *Corynebacterium glutamicum* |
| 4 | *Delftia acidovorans* |
| 5 | *Pseudomonas stutzeri* |
| 6 | *Rhodococcus opacus* |
| 7 | *Rhodococcus ruber* |
| 8 | *Pseudomonas putida* |
| 9 | *Rhodococcus jostii* |
| 10 | *Yarrowia lipolytica* |
| 11 | *Yarrowia lipolytica* |
| 12 | *Rhodococcus rhodochrous* |
| 13 | *Sphingopyxis witflaiensis* |
| 14 | *Streptomyces venezuelae* |
| 15 | *Pseudomonas* sp. Rh926 |
| 16 | *Brevundimonas vesicularis* |
| 17 | *Bacillus megaterium* |
| 18 | *Sphingomonas* sp. PWEI |
| 19 | *Candida maltose* |
| 20 | *Brevibacillus formosu* |
| 21 | *Cobetia marina* |

Figure 7:
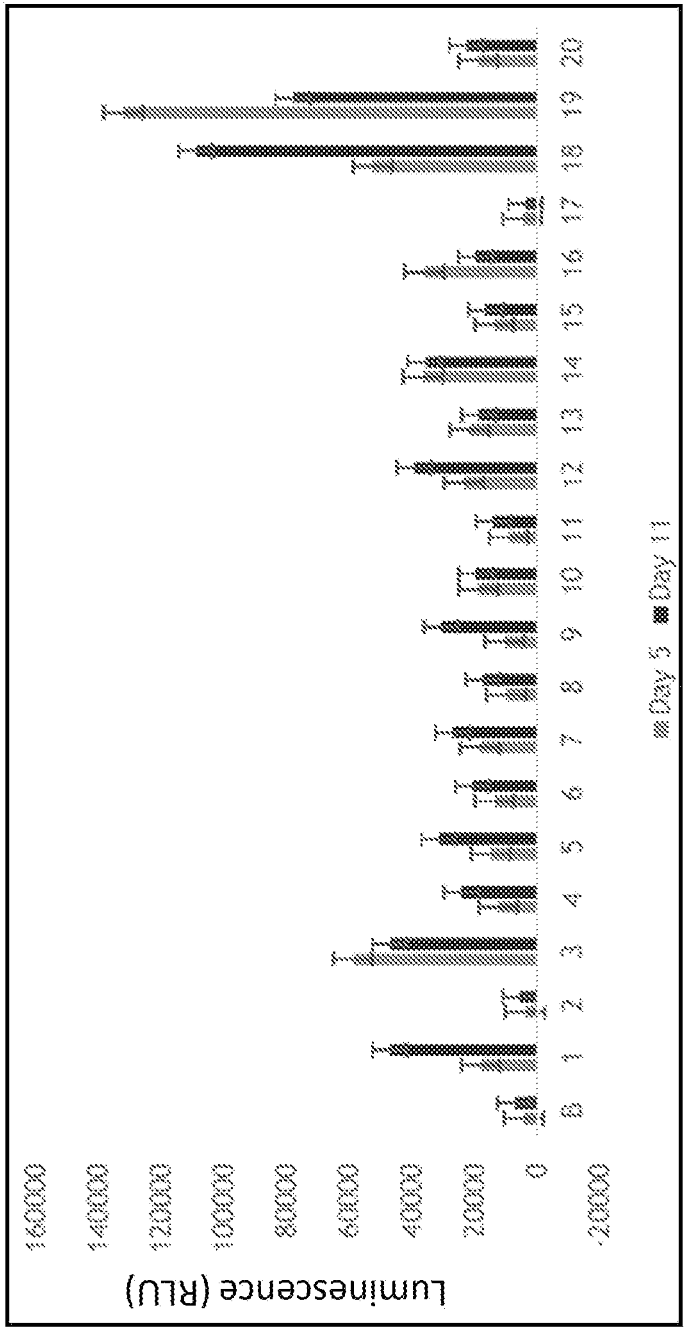
FIG. 7 is a graph illustrating luminescence in relative luminescence units versus various microbial strains in accordance with Example 8.
Figure 8:
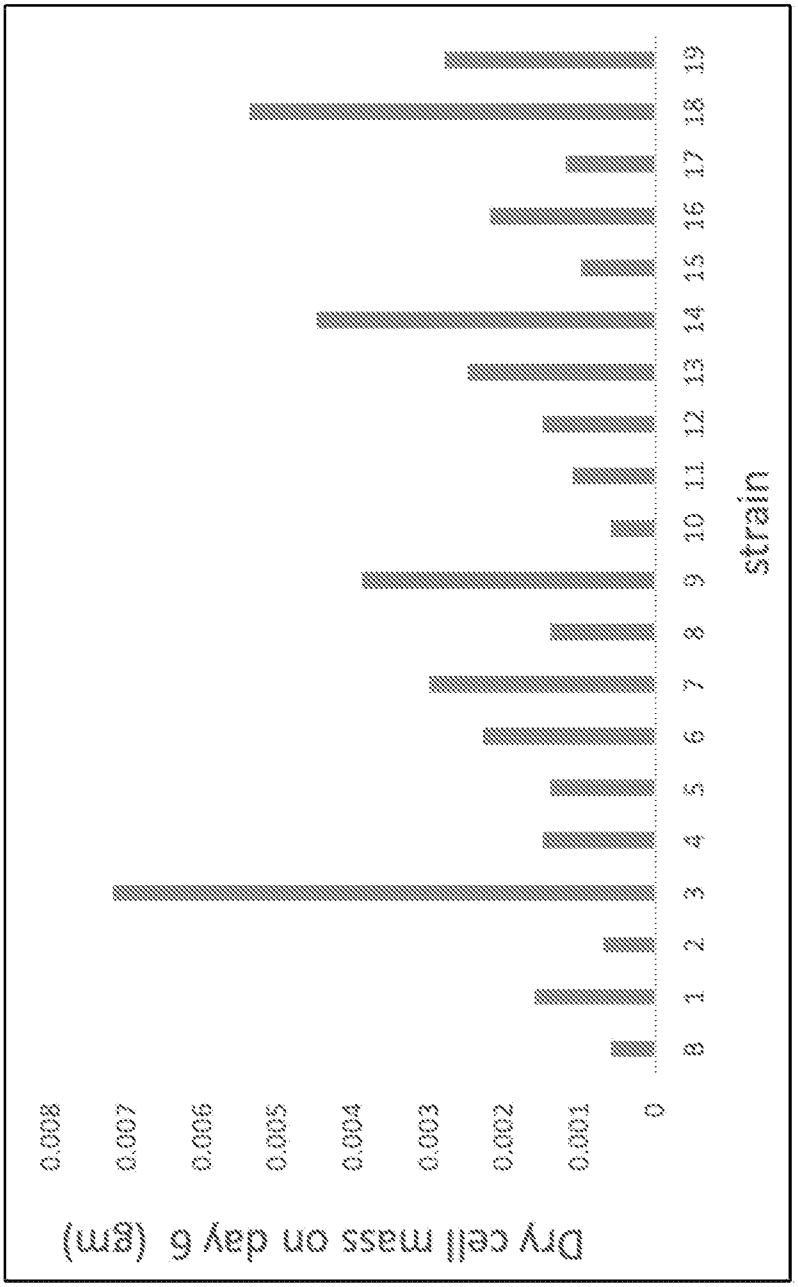
FIG. 8 is a graph illustrating dry cell mass in grams versus various microbial strains in accordance with Example 8.

Aliquots of each of the test samples were subjected to a cell viability assay (Bactiter Glo). Using the Bactiter Glo cell viability assay, luminescence of the samples is proportional to adenosine triphosphate (ATP) concentration. Because ATP is proportionally related to live cell concentration, higher ATP concentrations indicate higher live cell concentrations. FIG. 7 provides a graphical illustration of the luminescence of the samples after 5 days and 11 days of incubation versus the luminescence of blank sample medium with no cells (labeled as "B" on the x-axis). Several organisms exhibited growth with the depolymerized substrate as the sole carbon source. The highest levels of growth were measured for *Exophiala alcalophila, Corynebacterium glutamicum, Sphingomonas* sp. PWE1, and *Candida maltosa*. As a further assessment of cellular growth, the dry cell masses for the incubated samples after 5 days of growth are shown in FIG. 8.

Example 9. Biological Availability of Depolymerized PE in the Presence of Glucose The depolymerized substrate from Example 1 was added at 2 mg/mL into a minimal medium containing yeast nitrogen base and 2 mg/mL glucose (Glc) at pH 7. The samples (0.5 mL) were then individually inoculated with a monoculture of one of the microbial strains into a 96-well plate. Control samples included depolymerized PE in base media in absence of glucose, 2 mg/mL glucose in base media, and base media alone.

Figure 9:
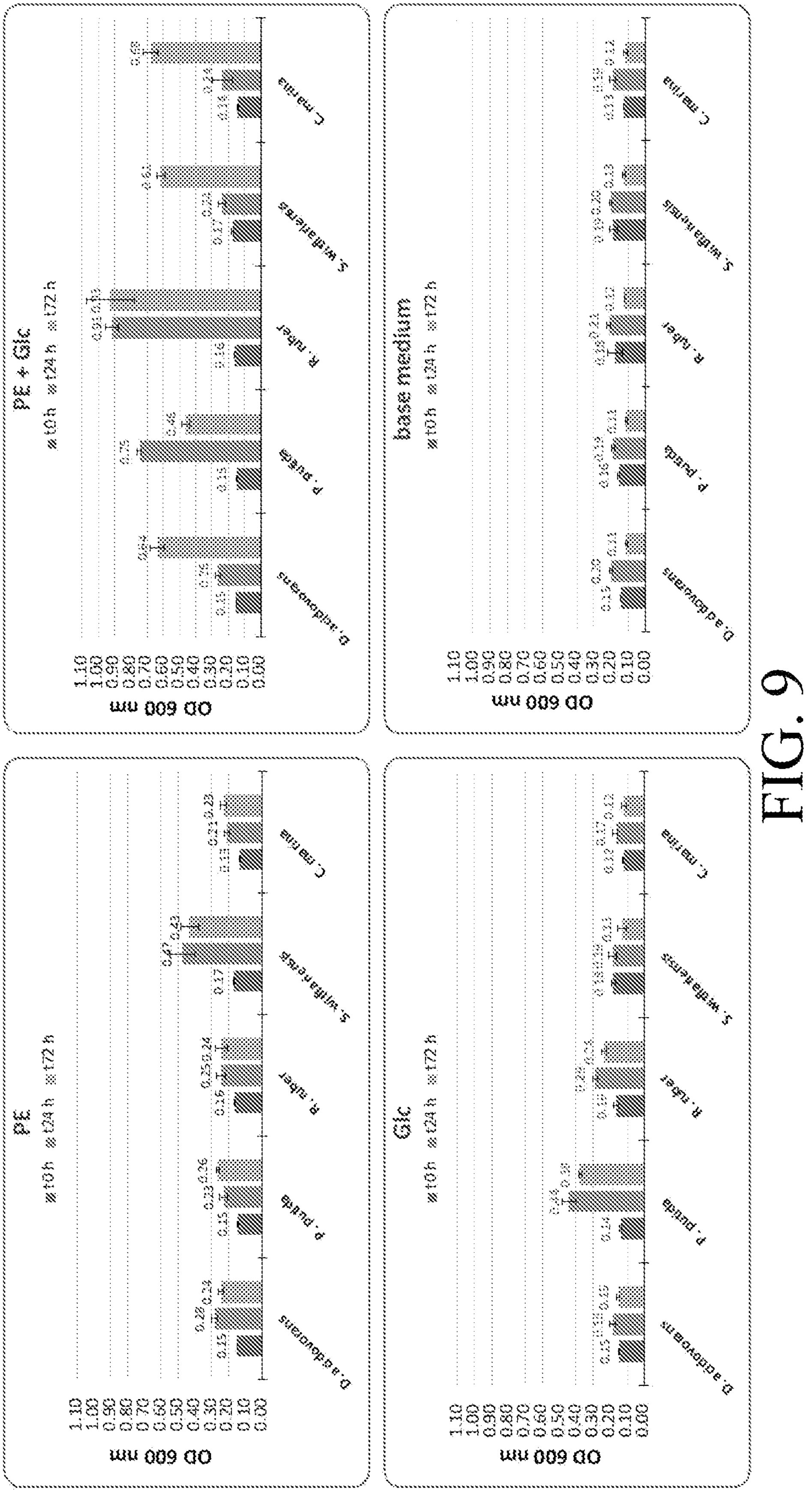
FIG. 9 is a graph illustrating optical density at 600 nanometers versus various microbial strains at zero, 24 and 72 hours in accordance with Example 9.

FIG. 9 provides a graphical illustration of the optical density at 600 nanometers for the 5 microbial strains tested and for the control samples. The optical density was measured at the start of the assay ("t0 h") and after 24 hours ("t24 h") and after 72 hours ("t72 h"). Growth on the depolymerized LDPE in the presence of glucose was much greater than for the control with glucose and base media for *D. acidovorans, R. ruber, S. witflariensis*, and *C. marina*. In comparison to the growth medium alone the presence of the depolymerized PE alone increased the optical density for the same organisms as well as for *P. putida.*

Example 10. Biological Availability of Depolymerized PE for Three pH Values

The depolymerized substrate from Example 4 was diluted into a minimal medium. The minimal medium contained the following components per liter: 0.05 g yeast extract, 0.5 g $KH_2PO_4$, 0.5 g $K_2HPO_4$, 2.5 g $(NH_4)_2SO_4$, 0.1 g NaCl, 0.01 g $FeSO_{4-7}H_2O$, 0.004 g $MnSO_4$—$H_2O$, 0.6 g $MgSO_4$-$7H_2O$, 0.02 g $CaCl_2$-$2H_2O$. Four samples were then adjusted to pH values of 3, 7, 8 and 10. These were individually inoculated with a monoculture of strain 16, *Brevundimonas vesicularis.*

Figure 10:
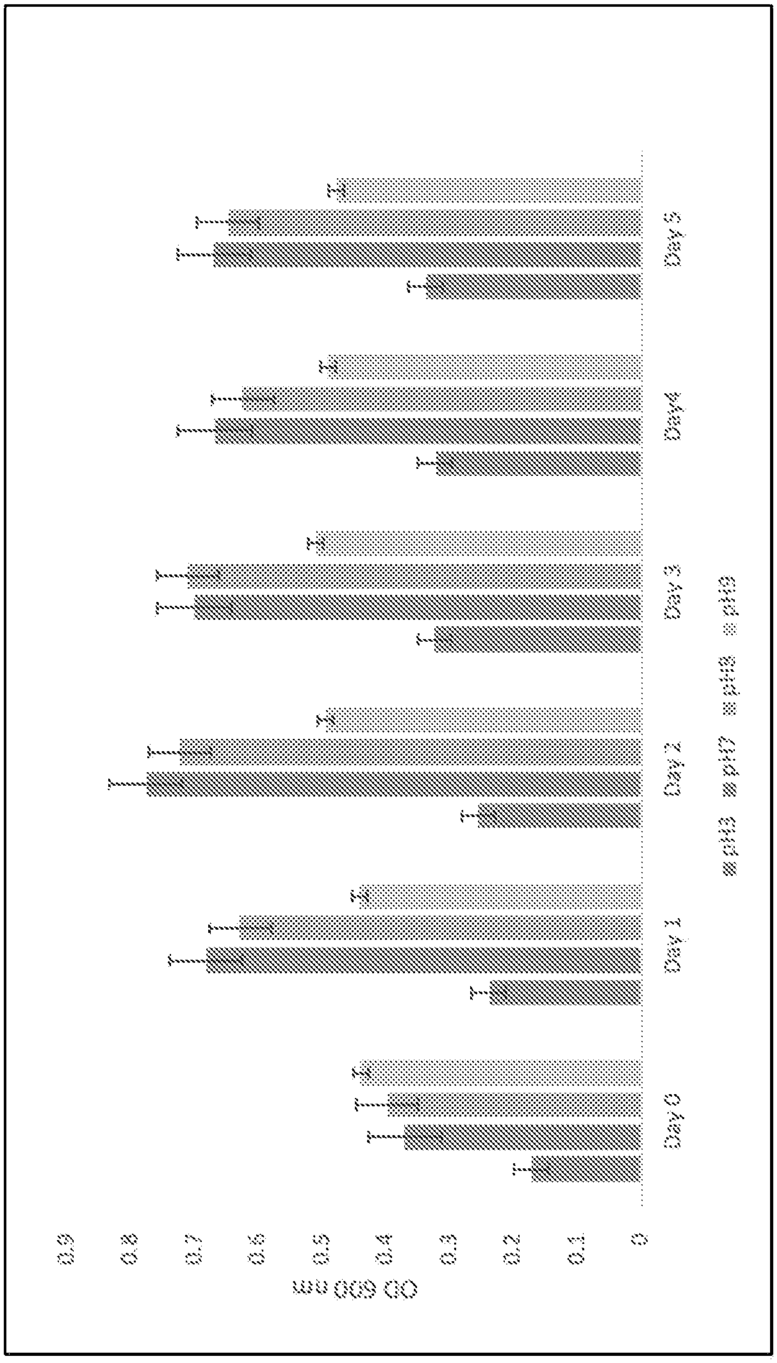
FIG. 10 is a graph illustrating optical density at 600 nanometers versus days for various pH conditions in accordance with Example 10.

FIG. 10 provides a graphical illustration of the optical density at 600 nanometers for strain 16 at the four pH values. The strongest growth was observed at pH 7 and pH 8.

Figure 11:
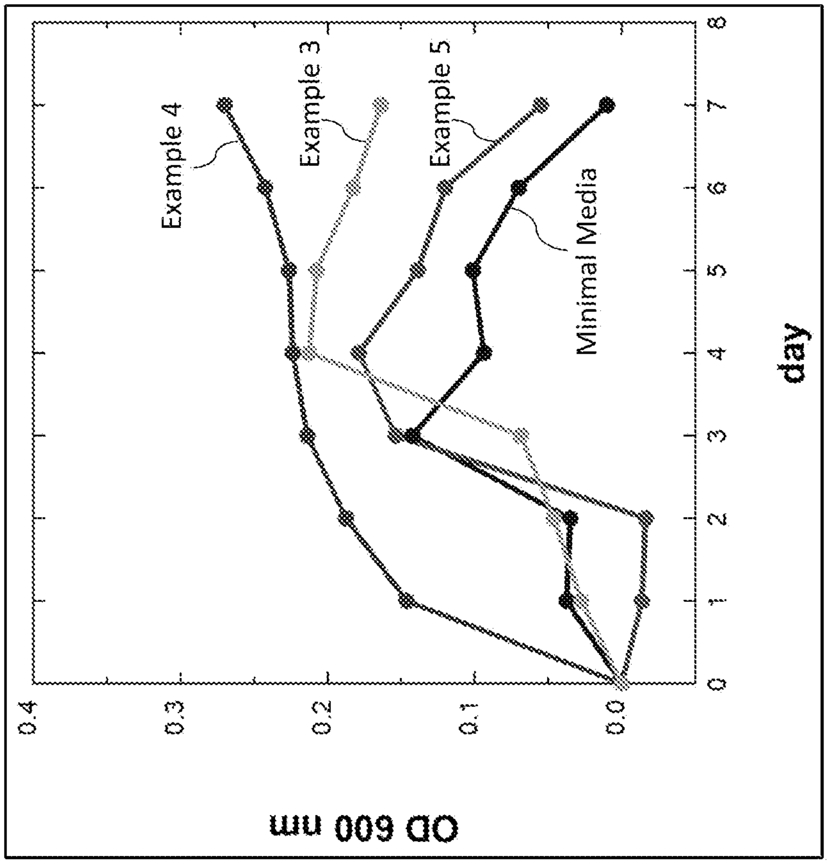
FIG. 11 is a graph illustrating optical density at 600 nanometers versus days in accordance with Example 11.

Example 11. Biological Availability of Depolymerized PE for Three C/S Ratios The depolymerized substrate from Examples 4-6 were individually diluted into a minimal medium. For these three depolymerized substrates, the C/S ratios prior to the bond cleavage step were 4.8, 10.2, and 16, respectively (Table 2). The minimal medium contained the following components per liter: 0.05 g yeast extract, 0.5 g $KH_2PO_4$, 0.5 g $K_2HPO_4$, 2.5 g $(NH_4)_2SO_4$, 0.1 g NaCl, 0.01 g $FeSO_4$-$7H_2O$, 0.004 g $MnSO_4$—$H_2O$, 0.6 g $MgSO_4$-$7H_2O$, 0.02 g $CaCl_2$-$2H_2O$. The three samples were individually inoculated with a monoculture of strain 16, *Brevundimonas vesicularis*. FIG. 11 provides a graphical illustration of the optical density at 600 nanometers for the three depolymerized PE samples over a 7-day period at pH 3.8. The best growth was observed for the depolymerized substrate of Example 4, with C/S ratio of 4.0. As the extent of depolymerization increases, the C/S ratio of the sulfonated polyolefin decreases. The increased depolymerization of the bioavailable carbon products of Example 4 increased the soluble product bioavailability in spite of the higher sulfur content of the breakdown products.

The disclosed method 100 provides a process to depolymerize a polyolefin efficiently and economically via sequential sulfonation and bond cleavage. The efficiency of the method 100 is illustrated by a carbon yield for the bioavailable carbon product 108 of about 50 wt % to about 80 wt % of the total carbon contained in the polyolefin 101 starting material. For economic considerations, the sulfonation reaction 103 of the method 100 can be performed with readily available reagents (e.g., fuming sulfuric acid) and with simple isolation techniques (e.g., filtration). The method 100 can be tailored to adjust product ratios of carbon dioxide to soluble and insoluble materials. Furthermore, the molecular weight composition of the soluble organic products (bioavailable carbon product 108) can be tailored to bioavailability. In some embodiments, the bioavailable carbon product 108 demonstrates bioavailability as a sole carbon source for various microbial strains.

Those of skill in the art will appreciate that various example embodiments are shown and described herein, each having certain features in the particular embodiments, but the present disclosure is not thus limited. Rather, the present disclosure can be modified to incorporate any number of variations, alterations, substitutions, combinations, sub-combinations, or equivalent arrangements not heretofore described, but which are commensurate with the scope of the present disclosure. Additionally, while various embodiments of the present disclosure have been described, it is to be understood that aspects of the present disclosure may include only some of the described embodiments. Accordingly, the present disclosure is not to be seen as limited by the foregoing description but is only limited by the scope of the appended claims.

What is claimed is:

1. A method for depolymerizing polyolefins, the method comprising:

a sulfonation step comprising contacting a polyolefin with a sulfonating agent in the absence of an organic solvent to provide a sulfonated polyolefin and a reaction mixture;

a bond cleavage step comprising contacting a metal catalyst and an oxidant with the sulfonated polyolefin, wherein a carbon-carbon bond of the sulfonated polyolefin is cleaved to provide a bioavailable carbon product;

wherein the bioavailable carbon product is a carbon source for microbial growth;

the metal catalyst is added to an aqueous dispersion of the sulfonated polyolefin to provide a metal-loaded sulfonated polyolefin, the metal-loaded sulfonated polyolefin is isolated by filtration, rinsed with water to remove excess metal catalyst.

2. The method of claim 1, wherein the sulfonating agent is a sulfur oxo acid.

3. The method of claim 2, wherein the sulfonating agent is fuming sulfuric acid, sulfuric acid, polysulfuric acid, dithionic acid, or combinations thereof.

4. The method of claim 1, wherein the polyolefin is high-density polyethylene, poly(vinyl chloride), low-density polyethylene, polybutene, polymethylpentene, polypropylene, polystyrene, mixtures, co-polymers thereof, or combinations thereof.

5. The method of claim 1, wherein the sulfonated polyolefin has a carbon to sulfur (C/S) molar ratio of about 20 to about 3.

6. The method of claim 1, wherein the sulfonated polyolefin has a carbon to sulfur (C/S) molar ratio of about 17 to about 5.

7. The method of claim 1, wherein the metal catalyst is a Fe(II) salt, a Fe(III) salt, a Cu(I) salt, a Cu(II) salt, a Cu(III) salt, a Mn(II) salt, a Mn(III) salt, or a combination thereof.

8. The method of claim 1, wherein the oxidant is $H_2O_2$, $O_2$, or a combination thereof.

9. The method of claim 1, wherein the bond cleavage step has a metal to sulfur (M/S) molar ratio of about 0.01 to about 2.

10. The method of claim 1, wherein in the bond cleavage step there is an oxidant to monomer molar ratio of about 1 to about 10, wherein the oxidant is moles of oxidant in the oxidation step and the monomer is moles of monomer in the polyolefin.

11. The method of claim 1, wherein during the bond cleavage step, the metal catalyst is added to an aqueous dispersion of the sulfonated polyolefin to provide a metal-loaded sulfonated polyolefin, followed by addition of the oxidant without removal of excess metal catalyst.

12. The method of claim 1, wherein during the bond cleavage step, the metal-loaded sulfonated polyolefin after being isolated by filtration, and rinsed with water to remove excess metal catalyst is dried prior to addition of the oxidant.

13. The method of claim 1, wherein less than about 60% of total carbon in the polyolefin is converted into carbon dioxide.

14. A method for depolymerizing polyolefins, the method comprising:

a sulfonation step comprising contacting a polyolefin with a sulfonating agent in the absence of an organic solvent to provide a sulfonated polyolefin and a reaction mixture;

a bond cleavage step comprising contacting a metal catalyst and an oxidant with the sulfonated polyolefin, wherein a carbon-carbon bond of the sulfonated polyolefin is cleaved to provide a bioavailable carbon product;

wherein the bioavailable carbon product is a carbon source for microbial growth;

wherein an M/S molar ratio is 0.02 to 0.3, wherein M is a molar amount of metal present in the metal catalyst and S is a molar amount of sulfur present in the sulfonated polyolefin, an oxidant to monomer molar ratio is 1.4 to 2.6, wherein the oxidant is moles of oxidant in the oxidation step and the monomer is moles of monomer in the polyolefin, and a yield of bioavailable carbon is 20% to 60% of the carbon in the polyolefin.

15. The method of claim 1, further comprising combining a reaction product resulting after the metal-loaded sulfonated polyolefin is isolated by filtration, and rinsed with water to remove excess metal catalyst with an organism selected from the group consisting of: *Exophiala alcalophila, Corynebacterium glutamicum, Pseudomonas stutzeri, Pseudomonas putida, Rhodococcus jostii, Yarrowia lipolytica, Rhodococcus rhodochrous, Rhodococcus ruber, Streptomyces venezuelae, Pseudomonas* sp. Rh926, *Brevundimonas vesicularis, Sphingomonas* sp. PWE1, *Candida maltosa, Delftia acidovorans, Sphyingopyxis wiflariensis*, and *Cobetia marina.*

16. The method of claim 1, wherein the polyolefin is in a form of a film.

* * * * *